United States Patent
Platzek et al.

[11] Patent Number: 5,919,433
[45] Date of Patent: Jul. 6, 1999

[54] MACROCYCLIC METAL COMPLEX CARBOXYLIC ACIDS, THEIR USE AS WELL AS PROCESS FOR THEIR PRODUCTION

[75] Inventors: Johannes Platzek; Bernd Radüchel; Heribert Schmitt-Willich, all of Berlin, Germany

[73] Assignee: Schering Aktiengesellschaft, Germany

[21] Appl. No.: 08/982,579

[22] Filed: Dec. 2, 1997

Related U.S. Application Data

[60] Provisional application No. 60/032,988, Dec. 13, 1996.

[30] Foreign Application Priority Data

Dec. 4, 1996 [DE] Germany .................. 196 52 387

[51] Int. Cl.$^6$ .................................................. A61B 5/055
[52] U.S. Cl. ..................... 424/9.365; 534/16; 540/465; 540/474; 514/184; 514/836
[58] Field of Search ................. 424/9.365; 534/16; 540/465, 474; 514/184, 836; 436/173; 600/420

[56] References Cited

U.S. PATENT DOCUMENTS

| | | | |
|---|---|---|---|
| 5,162,109 | 11/1992 | Rajagopalan et al. | 424/1.1 |
| 5,277,895 | 1/1994 | Platzek et al. | 424/9 |
| 5,508,388 | 4/1996 | deLearie et al. | 534/16 |
| 5,573,752 | 11/1996 | Ranganathan et al. | 424/9.363 |
| 5,649,537 | 7/1997 | Anelli et al. | 128/653.4 |

FOREIGN PATENT DOCUMENTS

97/30969  8/1997  WIPO.

*Primary Examiner*—Gary E. Hollinden
*Attorney, Agent, or Firm*—Millen, White, Zelano & Branigan, P.C.

[57] ABSTRACT

The invention relates to new macrocyclic metal complex carboxylic acids of formula II

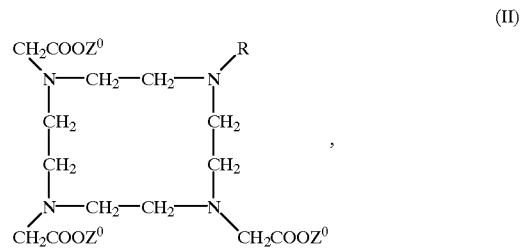

(II)

whereby $Z^0$ stands for a metal ion equivalent of atomic numbers 58–71 and

R stands for a $CHX^1$—CO—NH—$CHY^1$—$(CH_2)_f$—COOH group, in which $X^1$ and $Y^1$, independently of one another, mean a hydrogen atom, a straight-chain or branched $C_1$–$C_7$ alkyl radical, a phenyl or benzyl group and f means numbers 0 to 9.

They can be used as intermediate stages for synthesis of cascade polymer complexes that are suitable as diagnostic agents.

9 Claims, No Drawings

MACROCYCLIC METAL COMPLEX CARBOXYLIC ACIDS, THEIR USE AS WELL AS PROCESS FOR THEIR PRODUCTION

This application claims benefit of Provisional Application 60/032,988 filed Dec. 13, 1996.

The invention relates to the object characterized in the claims, i.e., new macrocyclic metal complex carboxylic acids, their use as well as process for their production.

Regarding the prior art, the following pages 1–23 from unpublished application PCT/EP 96/02671 are cited:

The contrast media that are now used in clinical practice for the modern imaging processes of nuclear spin tomography (MRI) and computer tomography (CT) [Magnevist$^{(R)}$, Pro Hance$^{(R)}$, Ultravist$^{(R)}$ and Omniscan$^{(R)}$] are dispersed in the entire extracellular space of the body (intravascular space and interstitium). This dispersion space comprises about 20% of the volume of the body.

In clinical practice, extracellular MRI contrast media were first used successfully in the diagnosis of cerebral and spinal disease processes since here a quite special situation exists with respect to the regional dispersion space. In the brain and spinal cord, extracellular contrast media in healthy tissue do not leave the intravascular space because of the blood-brain barrier. In the case of pathological processes with disruption of the blood-brain barrier (e.g., malignant tumors, inflammations, demyelinating diseases, etc.), regions with elevated blood-vessel permeability then develop inside the brain for these extracellular contrast media (Schmiedl et al., MRI of Blood-Brain Barrier Permeability in Astrocytic Gliomas: Application of Small and Large Molecular Weight Contrast Media, Magn. Reson. Med. 22: 288, 1991). Affected tissue can be identified with high contrast relative to healthy tissue by exploiting this disruption of vascular permeability.

Outside of the brain and the spinal cord, however, no such permeability barrier exists for the above-mentioned contrast media (Canty et al., First-Pass Entry of Nonionic Contrast Agent into the Myocardial Extravascular Space. Effects on Radiographic Estimate of Transit Time and Blood Volume. Circulation 84: 2071, 1991). Thus, the concentration of the contrast medium is no longer dependent on vascular permeability, but only on the size of the extracellular space in the corresponding tissue. Delimitation of the vessels relative to the surrounding interstitial space using this contrast medium is not possible.

A contrast medium that is dispersed exclusively in the vascular space would be desirable, particularly for the visualization of vessels. The purpose of such a blood-pool agent is to make it possible, with the aid of nuclear spin tomography, to delimit tissue with sufficient blood supply from tissue with insufficient blood supply, and thus to diagnose an ischemia. Infarcted tissue can also be delimited, based on its anemia, from surrounding healthy or ischemic tissue if a vasal contrast medium is used. This is of special importance if, e.g., the point is to distinguish a myocardial infarction from an ischemia.

To date, most of the patients in whom there is suspicion of cardiovascular disease (this disease is the most frequent cause of death in Western industrialized countries) have to undergo invasive diagnostic tests. In angiography at present, diagnostic radiology with the aid of-iodine-containing contrast media is used in particulars These tests suffer from various drawbacks: they are associated with the risk of radiation exposure, as well as with difficulties and stresses, which therefore particularly have the effect that the iodine-containing contrast media, as compared with NMR contrast media, have to be used in much higher concentrations.

There is therefore a need for NMR contrast media which can mark the vascular space (blood-pool agents) These compounds are to be distinguished by good compatibility and by high effectiveness (high increase of signal intensity with MRI).

Thus far, the attempt to solve at least a part of this problem by using complexes that are bound to macromolecules or biomolecules has been successful only to a very limited extent.

Thus, for example, the number of paramagnetic centers in the complexes that are described in European Patent Applications No. 0 088 695 and No. 0 150 844 is not sufficient for satisfactory imaging.

If the number of metal ions required is increased by repeated introduction of complexing units into a macromolecular biomolecule this is associated with an intolerable impairment of the affinity and/or specificity of this biomolecule [J. Nucl. Med. 24, 1158 (1983)]).

... intravenous injection in rats ... a concentration in the liver tissue that constitutes almost 30% of the dose. In addition, only 20% of the dose is eliminated in 24 hours.

The macromolecule polylysine-GdDTPA (European Patent Application, Publication No. 0 233 619) has also proved suitable as a blood-pool agents Because of production, however, this compound consists of a mixture of molecules of different sizes. In excretion tests in rats, it was shown that this macromolecule is excreted unchanged by glomerular filtration through the kidneys. Due to factors related to synthesis, however, polylysine-GdDTPA may also contain macromolecules that are so large that they cannot pass through the capillaries of the kidneys in the case of glomerular filtration and thus remain in the body.

Also, macromolecular contrast media based on carbohydrates, e.g., dextran, have been described (European Patent Application, Publication No. 0 326 226). The drawback of these compounds lies in the fact that the latter generally carry only about 5% of the signal-enhancing paramagnetic cation.

The polymers described in European Patent Application No. 0 430 863 already represent a step toward blood-pool agents since they no longer exhibit the size and molecular weight relative to heterogeneity that are characteristic of the previously mentioned polymers. They leave something to be desired, however, as regards complete elimination, compatibility, and/or effectiveness.

As described in PCT/EP 96/02671, it has been found that complexes which consist of nitrogen-containing cascade polymers that are provided with complexing ligands, at least 16 ions of an element of atomic numbers 20–29, 39, 42, 44 or 57–83, and optionally cations of inorganic and/or organic bases, amino acids or amino acid amides, and which optionally contain acylated amino groups are surprisingly very well suited for the production of NMR and x-ray diagnostic agents without exhibiting the mentioned drawbacks.

The complexing cascade polymers that are described in the indicated patent application can be described by general formula I $$A\text{-}\{X\text{-}[Y\text{-}(Z\text{-}(W\text{-}K_w)_z)_y]_x\}_a, \qquad (I)$$

in which

A stands for a nitrogen-containing cascade nucleus of base multiplicity a,

X and Y, independently of one another, stand for a direct bond or a cascade reproduction unit of reproduction multiplicity x or y, Z and W, independently of one another, stand for a cascade reproduction unit of reproduction multiplicity z or w, K stands for the radical of a complexing agent, a stands for numbers 2 to 12, x, y, z and w, independently of one another, stand for numbers 1 to 4, provided that at least two reproduction units are different and that $$16 < a \cdot x \cdot y \cdot z \cdot w < 64$$

holds true for the product of the multiplicities

As cascade nucleus A, the following are suitable-nitrogen atom,

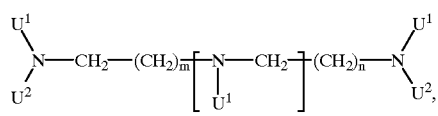

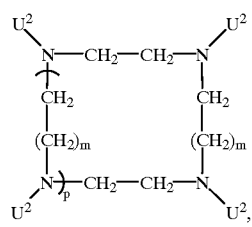

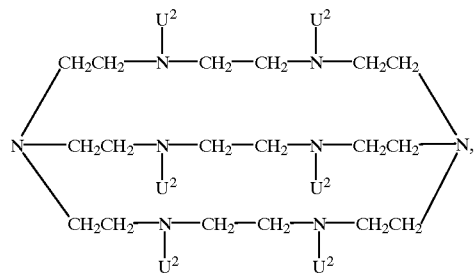

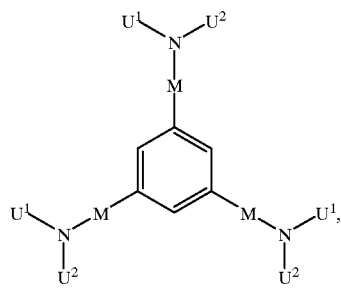

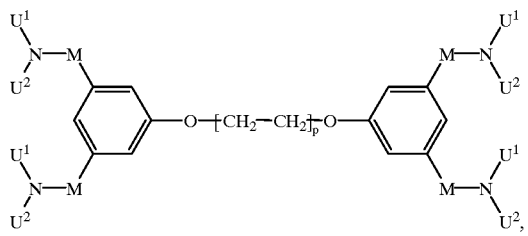

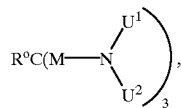

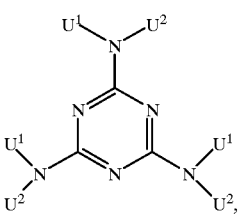

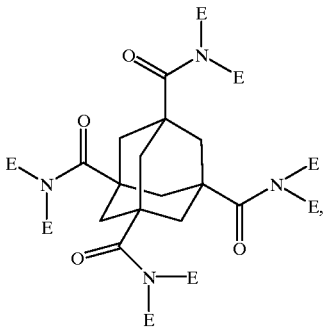

in which m and n stand for numbers 1 to 10, p stands for numbers 0 to 10, $U^1$ stands for $Q^1$ or E, $U^2$ stands for $Q^2$ or E with E meaning the group

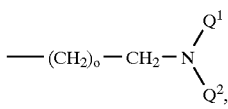

whereby o stands for numbers 1 to 6, $Q^1$ stands for a hydrogen atom or $Q^2$ and $Q^2$ stands for a direct bond, M stands for a $C_1$–$C_{10}$ alkylene chain which optionally is interrupted by 1 to 3 oxygen atoms and/or optionally is substituted with 1 to 2 oxo groups, $R^o$ stands for a branched or unbranched $C_1$–$C_{10}$ alkyl radical, a nitro, amino, carboxylic acid group or for

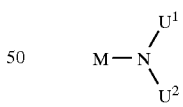

whereby number $Q^2$ corresponds to base multiplicity a.

The nitrogen atom, whose three bonds (base multiplicity a=3) in a first "inner layer" (generation 1) are occupied by three reproduction units X or Y (if X stands for a direct bond) or Z (if X and Y in each case stand for a direct bond), represents the simplest case of a cascade nucleus; in other words: the three hydrogen atoms of the basic cascade starter ammonia $A(H)_a = NH_3$ have been substituted by three reproduction units X or Y or Z. In this case, number $Q^2$ contained in cascade nucleus A represents base multiplicity a.

Reproduction units X, Y, Z and W contain —$NQ^1Q^2$ groups, in which $Q^1$ means a hydrogen atom or $Q^2$ and $Q^2$ means a direct bond. The number $Q^2$ contained in the respective reproduction unit (e.g., X) corresponds to the reproduction multiplicity of this unit (e.g., x in the case of X). The product of all multiplicities a·x·y·z·w indicates the number of complexing agent radicals K bound in the cascade polymers The polymers according to the invention contain at least 16 and at most 64 radicals K in the molecule, which in each case can bond one to a maximum of three (in the case of divalent ions), preferably one ion, to an element of the above-mentioned atomic numbers.

The last generation, i.e., reproduction unit W bound to complexing agent radical X, is bound to K with NH groups (—NQ$^1$Q$^2$ with Q$^1$ meaning a hydrogen atom and Q$^2$=direct bond), while the preceding reproduction units can be linked together both by NHQ$^2$ groups (e.g., by acylation reactions) and by NQ$^2$Q$^2$ groups (e.g., by alkylation reactions).

The cascade polymer complexes exhibit a maximum of 10 generations (ice., more than just one of reproduction units X, Y and Z can also be present in the molecule in each case), but preferably 2 to 4 generations, in which at least two of the reproduction units in the molecule are different.

As preferred cascade nuclei A, those are indicated which fall under the above-mentioned general formulas if m stands for numbers 1–3, especially preferably for number 1, n stands for numbers 1–3, especially preferably for number 1, p stands for numbers 0–3, especially preferably for number 1, o stands for number 1, M stands for a —CH$_2$, —CO or —CH$_2$CO group and R° stands for a —CH$_2$NU$^1$U$^2$, CH$_3$ or NO$_2$ group.

As further preferred cascade starters A(H)$_a$, there can be listed, e.g.:

(In the parentheses, base multiplicity a is indicated for the case where subsequent mono- or disubstitution is used in building the next generation)

Tris(aminoethyl)amine (a=6 or 3);
tris(aminopropyl)amine (a=6 or 3);
diethylenetriamine (a=5 or 3);
triethylenetetramine (a=6 or 4);
tetraethylenepentamine (a=7 or 5);
1,3,5-tris(aminomethyl)benzene (a=6 or 3);
trimesic acid triamide (a=6 or 3);
1,4,7-triazacyclononane (a=3);
1,4,7,10-tetraazacyclododecane (a=4);
1,4,7,10,13-pentaazacyclopentadecane (a=5);
1,4,8,11-tetraazacyclotetradecane (a=4);
1,4,7,10,13,16-hexaazacyclooctadecane (a=6);
1,4,7,10,13,16,19,22,25,28-decaazacyclotriacontane (a=10);
tetrakis(aminomethyl)methane (a=8 or 4);
1,1,1-tris(aminomethyl)ethane (a=6 or 3);
tris(aminopropyl)-nitromethane (a=6 or 3);
2,4,6-triamino-1,3,5-triazine (a=6 or 3);
1,3,5,7-adamantanetetracarboxylic acid amide (a=8 or 4);
3,3',5,5'-diphenylether-tetracarboxylic acid amide (a=8 or 4);
1,2-bis[phenoxyethane]-3', 3", 5',5"-tetracarboxylic acid amide (a=8 or 4);
1,4,7,10,13,16,21,24-octaazabicyclo[8.8.8]hexacosane (a=6).

It can be pointed out that the definition as cascade nucleus A and thus the separation of cascade nucleus and first reproduction unit can be selected by purely formal means and thus independently of the actual synthesis of the desired cascade polymer complexes. Thus, e.g., the tris(aminoethyl) amine used in Example 4 can be considered as cascade nucleus A itself (compare the general formula, indicated first for A, with m=n=p=U$^1$=E with o meaning number 1 and U$^1$=U$^2$=Q$^2$) but also as a nitrogen atom (=cascade nucleus A), which as a first generation exhibits three reproduction units

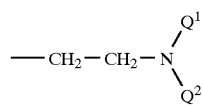

(compare the definition of E).

Cascade reproduction units X, Y, Z and W are determined, independently of one another, by

E,

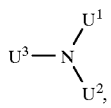

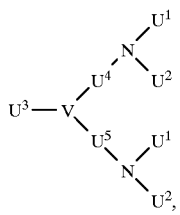

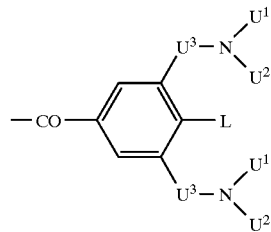

in which

U$^1$ stands for Q$^1$ or E,

U$^2$ stands for Q$^2$ or E with

E meaning the group

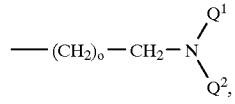

whereby o stands for numbers 1 to 6,

Q$^1$ stands for a hydrogen atom or Q$^2$,

Q$^2$ stands for a direct bond,

U$^3$ stands for a C$_1$–C$_{20}$ alkylene chain, which optionally is interrupted by 1 to 10 oxygen atoms and/or 1 to 2 —N(CO)$_q$—R$^2$ radicals, 1 to 2 phenylene radicals and/or 1 to 2 phenylenoxy radicals and/or optionally is substituted by 1 to 2 oxo, thioxo, carboxy, C$_1$–C$_5$ alkylcarboxy, C$_1$–C$_5$ alkoxy, hydroxy, C$_1$–C$_5$ alkyl groups, whereby q stands for numbers 0 or 1 and $R^2$ stands for a hydrogen atom, a methyl or an ethyl radical, which optionally is substituted with 1–2 hydroxy or 1 carboxy group(s), L stands for a hydrogen atom or the group

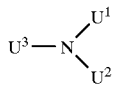

V stands for methine group

if at the same time $U^4$ means a direct bond or group M and $U^5$ has one of the meanings of $U^3$ or V stands for group

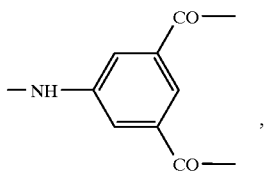

if at the same time $U^4$ and $U^5$ are identical and mean the direct bond or group M.

Preferred cascade reproduction units X, Y, Z and W are those in which in the above-mentioned general formulas, radical $U^3$ stands for —CO—, —COCH$_2$OCH$_2$CO—, —COCH$_2$—, —CH$_2$CH$_2$—, —CONHC$_6$H$_4$—, —COCH$_2$CH$_2$CO—, —COCH$_2$—CH$_2$CH$_2$CO—, —COCH$_2$CH$_2$CH$_2$CH$_2$CO—, radical $U^4$ stands for a direct bond, for —CH$_2$CO—, radical $U^5$ stands for a direct bond, for —(CH$_2$)$_4$—, —CH$_2$CO—, —CH(COOH)—, CH$_2$OCH$_2$CH$_2$—, —CH$_2$C$_6$H$_4$—, —CH$_2$—C$_6$H$_4$OCH$_2$CH$_2$—, radical E stands for a group

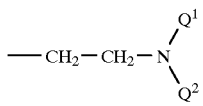

Cascade reproduction units X, Y, Z and W that are mentioned as examples can be cited:

—CH$_2$CH$_2$NH—; —CH$_2$CH$_2$N<;
—COCH(NH—)(CH$_2$)$_4$NH—; —COCH(N<)(CH$_2$)$_4$N<
—COCH$_2$OCH$_2$CON(CH$_2$CH$_2$NH—)$_2$;
—COCH$_2$OCH$_2$CON(CH$_2$CH$_2$N<)$_2$;
—COCH$_2$N(CH$_2$CH$_2$NH—)$_2$; —COCH$_2$N(CH$_2$CH$_2$N<)$_2$;
—COCH$_2$NH—; —COCH$_2$N<;
—COCH$_2$CH$_2$CON(CH$_2$CH$_2$NH—)$_2$;
—COCH$_2$CH$_2$CON(CH$_2$CH$_2$N<)$_2$;
—COCH$_2$OCH$_2$CONH—C$_6$H$_4$—CH[CH$_2$CON(CH$_2$CH$_2$NH—)$_2$]$_2$;
—COCH$_2$OCH$_2$CONH—C$_6$H$_4$—CH[CH$_2$CON(CH$_2$CH$_2$N<)$_2$]$_2$;
—COCH$_2$CH$_2$CO—NH—C$_6$H$_4$—CH[CH$_2$CON(CH$_2$CH$_2$NH—)$_2$]$_2$;
—COCH$_2$CH$_2$CO—NH—C$_6$H$_4$—CH[CH$_2$CON(CH$_2$CH$_2$N<)$_2$]$_2$;
—CONH—C$_6$H$_4$—CH[CH$_2$CON(CH$_2$CH$_2$NH—)$_2$]$_2$;
—CONH—C$_6$H$_4$—CH[CH$_2$CON(CH$_2$CH$_2$N<)$_2$]$_2$;
—COCH(NH—)CH(COOH)NH—; —COCH(N<)CH(COOH)N<;

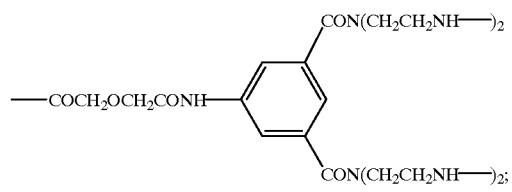

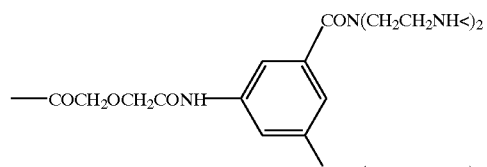

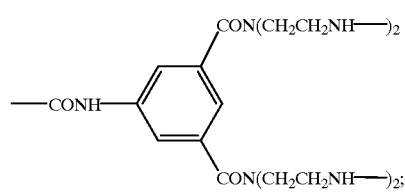

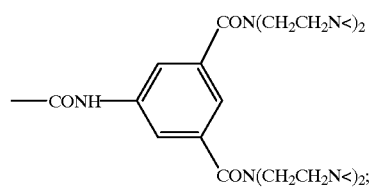

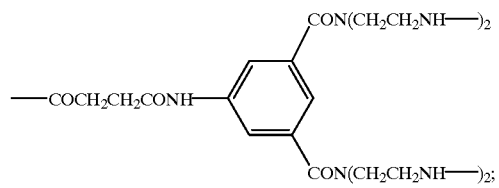

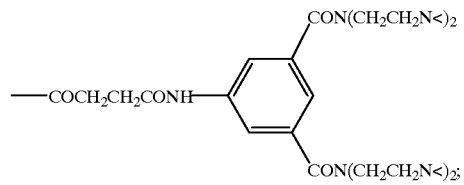

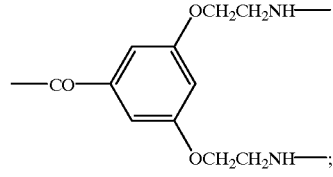

-continued

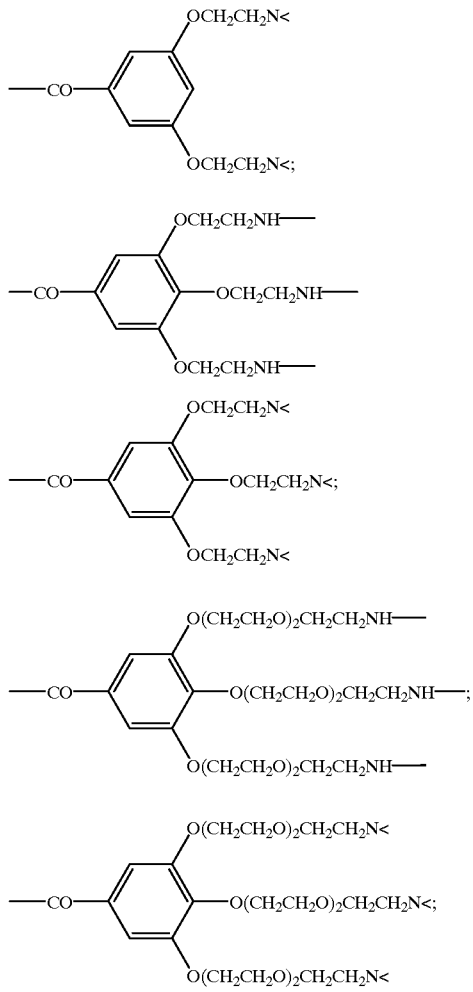

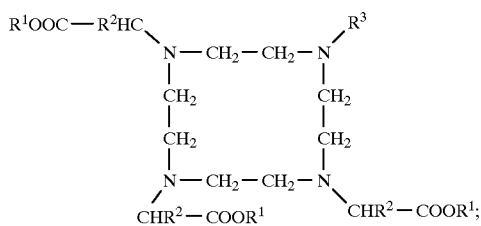

In the case of a macrocycle, completing agent radical K is described by general formula IA:

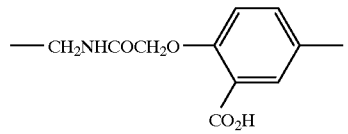

(IA)

in which $R^1$, independently of one another, stand for a hydrogen atom or a metal ion equivalent of atomic numbers 20–29, 39, 42–44 or 57–83, $R^2$ stands for a hydrogen atom, a methyl or an ethyl radical which optionally is substituted with 1–2 hydroxy or 1 carboxy group(s), $R^3$ stands for a $$-CH(R^4)-CO-N(R^2)-U^6-T$$

group, $R^4$ stands for a straight-chain, branched, saturated or unsaturated $C_1$–$C_{30}$ alkyl chain, which optionally is interrupted by 1–10 oxygen atoms, 1 phenylene group, 1 phenylenoxy group and/or optionally substituted by 1–5 hydroxy, 1–3 carboxy, 1-phenyl group(s), $U^6$ stands for a straight-chain, branched, saturated or unsaturated $C_1$–$C_{20}$ alkylene group optionally containing 1–5 imino, 1–3 phenylene, 1–3 phenylenoxy, 1–3 phenylenimino, 1–5 amide, 1–2 hydrazide, 1–5 carbonyl, 1–5 ethylenoxy, 1 urea, 1 thiourea, 1–2 carboxyalkylimino, 1–2 ester groups; 1–10 oxygen, 1–5 sulfur and/or 1–5 nitrogen atom(s) and/or optionally substituted by 1–5 hydroxy, 1–2 mercapto, 1–5 oxo, 1–5 thioxo, 1–3 carboxy, 1–5 carboxyalkyl, 1–5 ester and/or 1–3 amino group(s), whereby the phenylene groups that optionally can be contained can be substituted by 1–2 carboxy, 1–2 sulfo or 1–2 hydroxy groups, T stands for a —CO—α, —NHCO—α or —NHCS—α group, and α stands for the bonding site to the terminal nitrogen atoms of the last.

As preferred complexing agent radicals K, those can be mentioned in which in above-indicated formula IA, the $C_1$–$C_{20}$, and preferably $C_1$–$C_{12}$ alkylene chain that stands for $U^6$ contains the groups —$CH_2$—, —$CH_2NHCO$—, —$NHCOCH_2O$—, —$NHCOCH_2OC_6H_4$—, —$N(CH_2CO_2H)$—, —$NHCOCH_2C_6H_4$—, —$NHCSNHC_6H_4$—, —$CH_2OC_6H_4$—, —$CH_2CH_2O$— and/or is substituted by groups —COOH, —$CH_2COOH$.

As examples of $U^6$, the following groups can be cited,

—$CH_2$—, —$CH_2CH_2$—, —$CH_2CH_2CH_2$—, —$C_6H_4$—, —$C_6H_{10}$—, —$CH_2C_6H_5$—,

—$CH_2NHCOCH_2CH(CH_2CO_2H)$—$C_6H_4$—,

—$CH_2NHCOCH_2OCH_2$—,

—$CH_2NHCOCH_2C_6H_4$—,

—$CH_2NHCOCH_2O$—⟨C_6H_3(CO_2H)⟩—,

—$CH_2NHCSNH$—$C_6H_4$—$CH(CH_2COOH)CH_2$—,

—$CH_2OC_6H_4$—$N(CH_2COOH)CH_2$—,

—$CH_2NHCOCH_2O(CH_2CH_2O)_4$—$C_6H_4$—,

—$CH_2O$—$C_6H_4$—,

—$CH_2CH_2$—O—$CH_2CH_2$—, —$CH_2CH_2$—O—$CH_2CH_2$—O—$CH_2CH_2$—,

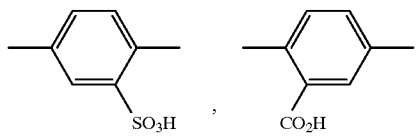

As examples of $R^4$ the following groups can be indicated:
—$CH_3$, —$C_6H_5$, —$CH_2$—COOH,
—$CH_2$—$C_6H_5$, —$CH_2$—O—($CH_2CH_2$—O—)$_6CH_3$,
—$CH_2$—OH If the agent is intended for use in NMR diagnosis, the central ion of the complex salt must be paramagnetic. These are especially the divalent and trivalent ions of the elements of atomic numbers 21–29, 42, 44, and 58–70. Suitable ions are, for example, the chromium(III), iron(II), cobalt(II), nickel(II), copper(II), praseodymium(III), neodymium(III), samarium(III), and ytterbium(III) ions. Because of their very strong magnetic moment, the gadolinium(III), terbium(III), dysprosium(III), holmium(III), erbium(III), manganese(II), and iron(III) ions are especially preferred.

If the described agent is intended for use in diagnostic radiology, the central ion has to be derived from an element of higher atomic number in order to achieve sufficient absorption of the x rays. It has been found that for this purpose, diagnostic agents which contain a physiologically compatible complex salt with central ions of elements of atomic numbers between 21–29, 39, 42, 44 and 57–83 are suitable; these are, for example, the lanthanum(III) ion and the above-mentioned ions of the lanthanide series.

The cascade polymer complexes contain at least 16 ions of an element of the above-mentioned atomic numbers.

The remaining acid hydrogen atoms, i.e., those which were not substituted by the central ion, optionally can be replaced completely or partially by cations of inorganic and/or organic bases, amino acids, or amino acid amides.

Suitable inorganic cations are, for example, the lithium ion, the potassium ion, the calcium ion, the magnesium ion, and especially the sodium ion. Suitable cations of organic bases are, i.a., those of primary, secondary, or tertiary amines, such as, for example, ethanolamine, diethanolamine, morpholine, glucamine, N,N-dimethylglucamine, and especially N-methylglucamine. Suitable cations of amino acids are, for example, those of lysine, arginine, and ornithine, as well as the amides of otherwise acidic or neutral amino acids The compounds which have a molecular weight of 10,000–80,000 D, preferably 15,000–40,000 D, exhibit the desired properties described above. They contain the large number, required for their use, of metal ions bound in a stable manner in the complex.

They accumulate in regions with high vascular permeability, such as, e.g., in tumors, they make it possible to make statements regarding the perfusion of tissues, and they provide the possibility of determining the blood volume in tissues, of shortening selectively the relaxation times or densities of the blood, and of graphically representing the permeability of blood vessels. Such physiological data cannot be obtained through the use of extracellular contrast media, such as, e.g., Gd-DTPA [Magnevist$^{(R)}$] From these standpoints, there also follow the uses in the modern imaging processes of nuclear spin tomography and computer tomography: more specific diagnoses of malignant tumors, early therapy monitoring in cases where cytostatic, antiphlogistic, or vasodilative therapy is used, early identification of underperfused regions (e.g., in the myocardium), angiography in vascular diseases, and identification and diagnosis of (sterile or infectious) inflammations The described cascade polymer complexes are also extremely well suited for (interstitial and i.v.) lymphography.

As further advantages relative to extracellular contrast media, such as, e.g., Gd-DTPA [Magnevist$^{(R)}$], the greater effectiveness as contrast media for nuclear spin tomography (higher relaxivity) must be emphasized; this ensures a marked reduction of the diagnostically required dose. At the same time, the described contrast media can be formulated as solutions in an isoosmolar manner in the blood and thus reduce the osmotic stress of the body, which is reflected in a reduced toxicity on the part of the substance (higher toxic threshold). Smaller doses and higher toxic thresholds result in a significant increase of the reliability of contrast medium use in modern imaging processes.

In comparison with macromolecular contrast media based on carbohydrates, e.g., dextran (European Patent Application, Publication No. 0 326 226), which carry—as mentioned—generally only about 5% of the signal-enhancing paramagnetic cation, the polymer complexes exhibit a content of the paramagnetic cation of generally about 20%. Thus, the described macromolecules produce much better signal enhancement per molecule, which simultaneously has the effect that the dose necessary for nuclear spin tomography is considerably smaller relative to macromolecular contrast media based on carbohydrates These polymer complexes are large enough to be able to leave the vascular space only slowly, but at the same time small enough to be able to pass through the capillaries of the kidneys, which are 300–800 Å in size.

In comparison to the other mentioned polymer compounds of the prior art, the described cascade polymer complexes are distinguished by improved excretion behavior, greater effectiveness, greater stability, and/or better compatibility.

The production of the macrocyclic cascade polymer complexes is carried out in that compounds of general formula I'

in which

A stands for a nitrogen-containing cascade nucleus of base multiplicity a; X and Ye independently of one another, stand for a direct bond or a cascade reproduction unit of reproduction multiplicity x or y, Z and W, independently of one another, stand for a cascade reproduction unit of reproduction multiplicity z or w, a stands for numbers 2 to 12, x, y, z and w independently of one another, stand for numbers 1 to 4 and β stands for the bonding site of the terminal NH groups of the last generation, of reproduction unit W provided that at least two reproduction units are different, and that for the product of multiplicities, $16 \leq a \cdot x \cdot y \cdot z \cdot w \leq 64$, holds true, are reacted with a complex or complexing agent K' of general formula I'A

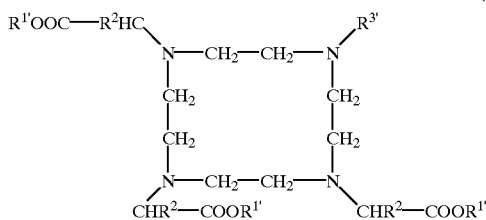

(I'A)

whereby

R[1]', independently of one another, stand for a hydrogen atom, a metal ion equivalent of atomic numbers 20–29, 39, 42–44, or 57–83 or an acid protective group, R[2] stands for a hydrogen atom, a methyl or an ethyl radical which optionally is substituted with 1–2 hydroxy or 1 carboxy group(s), R[3]' stands for a

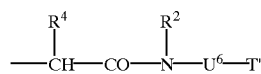

group,

R[4] stands for a straight-chain, branched, saturated or unsaturated $C_1$–$C_{30}$ alkyl chain, which optionally is interrupted by 1–10 oxygen atoms, 1 phenylene group, 1 phenylenoxy group and/or optionally substituted by 1–5 hydroxy, 1–3 carboxy, 1-phenyl group(s), U[6] stands for a straight-chain, branched, saturated or unsaturated $C_1$–$C_{20}$ alkylene group optionally containing 1–5 imino, 1–3 phenylene, 1–3 phenylenoxy, 1–3 phenylenimino, 1–5 amide, 1–2 hydrazide, 1–5 carbonyl, 1–5 ,thylenoxy, 1 urea, 1 thiourea, 1–2 carboxyalkylimino, 1–2 ,ster groups; 1–10 oxygen, 1–5 sulfur and/or 1–5 nitrogen atom(s) and/or optionally substituted by 1–5 hydroxy, 1–2 mercapto, 1–5 oxo, 1–5 thioxo, 1–3 carboxy, 1–5 carboxyalkyl, 1–5 ,ster and/or 1–3 amino group(s), whereby the phenylene groups that are optionally contained can be substituted by 1–2 carboxy, 1–2 sulfo or 1–2 hydroxy groups, T' stands for a —C*O, —COOH, —N=C=O or —N=C=S group, and C*O stands for an activated carboxyl group, provided that—if K' stands for a complex—at least two (in the case of divalent metals) or three (in the case of trivalent metals) of substituents R[1] stand for a metal ion equivalent of the above-mentioned elements and that optionally other carboxyl groups are present in the form of their salts with inorganic and/or organic bases, amino acids or amino acid amides, optionally present protective groups are cleaved, the cascade polymers that are thus obtained—if K' stands for a complexing agent—are reacted in a way known in the art with at least one metal oxide or metal salt of an element of atomic numbers 20–29, 39, 42, 44, or 57–83 and then optionally in the cascade polymer complexes that are thus obtained, acid hydrogen atoms that are still present are completely or partially substituted by cations of inorganic and/or organic bases, amino acids, or amino acid amides, and optionally still present free terminal amino groups are optionally acylated—before or after the metal complexing.

The reaction with complexing agents of general formula I'A, where R[1]'=t-butyl, is disclosed.

The production of the complexes and complexing agents of general formula I'A is carried out according to or analogously to the instructions described in the experimental part or according to methods known in the literature (see, e.g., European Patent Applications Nos. 0 512 661, 0 430 863, 0 255 471 and 0 565 930.

Thus, the production of compounds of general formula I'A is carried out, e.g., in that a group T'' is used as a precursor of functional group T', either in the meaning of a protected acid function, which can be converted to the free acid function independently of acid protective groups R[1]' according to the above-indicated process, or in the meaning of a protected amine function, which unblocks according to processes known in the literature [Th. W. Greene, P. G. M. Wuts, Protective Groups in Organic Synthesis, 2nd Edition, John Wiley & Sons (1991), pp. 309–385] and then can be converted into the isocyanates or isothiocyanates [Methoden der Org. Chemie [Methods of Organic Chemistry] (Houben-Weyl), E 4, pp. 742–749, 837–843, Georg Thieme Verlag, Stuttgart, New York (1983)]. Such compounds can be produced according to or analogously to the instructions that are described in the experimental part by monoalkylation of cyclene with suitable α-halogenated acid amides [in aprotic solvents, such as, e.g., chloroform].

For further details on coupling reactions, starting substances, introduction of the desired metal ions, production and administration of pharmaceutical agents, etc., please refer to WO 96/01655, ,specially pages 22 to 33.

This invention relates to new macrocyclic metal complex carboxylic acids of formula II

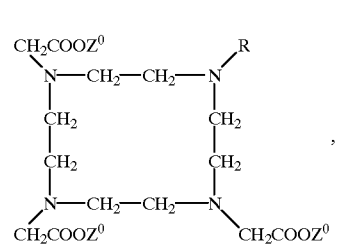

(II)

whereby

Z[o] stands for a metal ion equivalent of atomic numbers 58–71 and

R stands for a CHX[1]—CO—NH—CHY[1]—(CH$_2$)$_f$—COOH group, in which X[1] and Y[1], independently of one another, mean a hydrogen atom, a straight-chain or branched $C_1$—$C_7$ alkyl radical, a phenyl or benzyl group and f means numbers 0 to 9, which can be used as intermediate products for the synthesis of cascade polymer complexes of general formula I of PCT/EP 96/02671 and PCT/EP 95/02577.

For radical X[1] or Y[1], methyl, ethyl, propyl, butyl or hydrogen methyl, isopropyl phenyl and benzyl can be mentioned by way of example. Methyl or hydrogen is preferred Index f preferably stands for numbers 0, 1 or 2.

Of the above-mentioned lanthanides, gadolinium, dysprosium and ytterbium are preferred The reaction of the new macrocyclic metal complex carboxylic acids of formula II to the desired cascade polymer complexes is carried out analogously to methods that are known in the literature, e.g., B. Belleau, G. Malek, J. Amer. Chem. Soc. 90, 1651 (1968). The products that are thus obtained exhibit less by-product dispersion than the cascade polymer complexes that are synthesized without using the metal complex carboxylic acids of formula II according to the invention.

The synthesis of the compounds of general formula II according to the invention is carried out in that compounds of general formula III

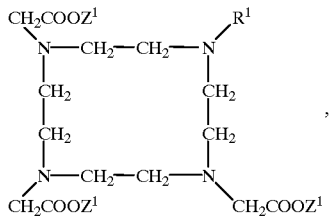
(III)

in which

R' has the meaning of R, whereby the carboxyl group contained therein is optionally present in protected form and $Z^1$ stands for a hydrogen atom or a carboxyl protective groups after cleavage of the optionally present carboxyl protective groups, are reacted in a way known in the art with a metal oxide or metal salt of an element of atomic numbers 58–71.

The introduction of the desired metal ions is carried out in the way in which it was disclosed in, e.g., Patents EP 71564, EP 130934 and DE-3401052, by the metal oxide or a metal salt (for example, the nitrate, acetate, carbonate, chloride or sulfate) of the element of atomic numbers 58–71 being dissolved or suspended in water and/or a lower alcohol (such as methanol, ethanol or isopropanol) and being reacted with a solution or suspension of the equivalent amount of complexing agent of general formula III.

If $Z^1$ stands for an acid protective group, e.g., straight-chain or branched $C_1$–$C_6$ alkyl, aryl and aralkyl groups, for example, the methyl, ethyl, propyl, butyl, phenyl, benzyl, diphenylmethyl, triphenylmethyl, bis(p-nitrophenyl)-methyl groups, as well as trialkylsilyl groups, are suitable. The t-butyl group is preferred.

The cleavage of the protective groups is carried out according to the processes known to one skilled in the art, by, for example, hydrolysis, hydrogenolysis, alkaline saponification of esters with alkali in aqueous-alcoholic solution at temperatures of 0° C. to 50° C., acid saponification with mineral acids or in the case of, e.g. tert-butyl esters with the aid of trifluoroacetic acid. [Protective Groups in Organic Synthesis, 2nd Edition, T. W. Greene and P. G. M. Wuts, John Wiley and Sons, Inc., New York, 1991].

Compounds of general formula III can be obtained by reaction of α-halocarboxylic acid esters or α-haloacids of general formula IV

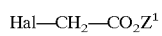
(IV), in which $Z^1$ has the above-mentioned meaning and Hal stands for chlorine, bromine or iodine, with compounds of general formula V

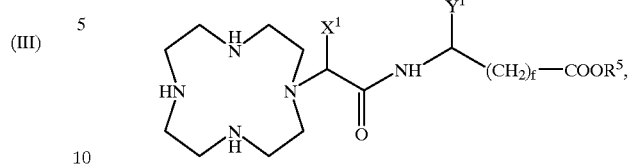
(V)

in which $R^5$ stands for a hydrogen atom, or an acid protective group and $X^1$, $Y^1$ and f have the above-mentioned meaning.

If $Z^1$ and $R^5$ in each case stand for an acid protective group, the latter can have varying meanings, so that $Z^1$ (e.g., benzyl) can be cleaved optionally selectively (e.g., by hydrolysis) in the presence of $R^5$ protective groups (e.g., t-butyl).

If $Z^1$ stands for an acid protective group, the reaction is carried out preferably is solvents such as methylene chloride, dimethylformamide, acetonitrile, tetrahydrofuran, dioxane, chloroform, lower alcohols such as methanol, ethanol and isopropanol, as well as mixtures of the above-mentioned solvents with water.

When a haloacid is used as an educt, water is the preferred working medium.

As acid traps, organic bases such as pyridine, triethylamine or diisopropylethylamine or inorganic bases such as sodium hydroxide, lithium hydroxide, potassium hydroxide, calcium hydroxide or sodium carbonate, potassium carbonate, sodium bicarbonate or lithium carbonate are used. Alkylation is performed at temperatures of between 0–100° C., but preferably at 20–80° C.

Compounds of general formula V are obtained by reaction of cyclene (formula VI)

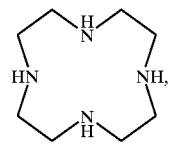
(VI)

with compounds of general formula VII

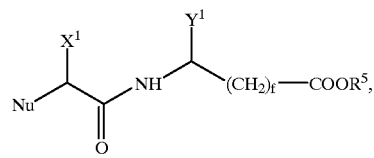
(VII)

in which $X^1$, $Y^1$, $R^5$ and f have the above-mentioned meaning and Nu stands for a nucleofuge. As nucleofuges, chloride, bromide, iodide, mesylate, tosylate or triflate can be mentioned.

The reaction is carried out in solvents such as chloroform methylene chloride, tetrahydrofuran, dioxane, dimethylformamide, dimethyl sulfoxide or else in water at temperatures of 0° C. to 100° C., but preferably at 20°–60°.

If desired an organic or inorganic base can be added. Triethylamine, pyridine, sodium carbonate, sodium hydroxide or potassium hydroxide can be mentioned by way of example.

Compounds of general formula VII are obtained by reaction of compounds of general formula VIII

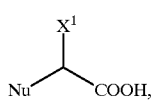

(VIII)

in which

Nu and $X^1$ have the above-mentioned meaning, with compounds of general formula IX

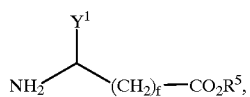

(IX)

in which $Y^1$, f and $R^5$ have the above-indicated meaning.

The reaction is carried out according to peptide-chemistry methods that are known to one skilled in the art. Thus, for example, a derivatives such as, e.g., an acid chloride, acid bromide or active ester (such as, e.g., NHS-ester) can be produced, for example, from the acid of general formula VIII, whereby said derivative is condensed with an amino acid (optionally terminally-protected).

Compounds of general formula VIII, as well as their acid chlorides and acid bromides are commercially available. Compounds of general formula IX are also commercially available as free amino acids or in protected form As an alternative, compounds of general formula III can be obtained by reaction of compounds of general formula X

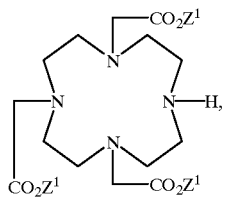

(X)

in which $Z^1$ has the above-mentioned meaning, with compounds of general formula VII, after cleavage of the optionally present acid protective groups.

The reaction is carried out in solvents, such as, for example, acetonitrile, dimethylformamide, tetrahydrofuran, dioxane or lower alcohols such as methanol, ethanol or i-propanol as well as mixtures of the latter with water; but the reaction can also be performed in pure water. The work is generally done at temperatures of 20° C.–100° C.

As acid traps, organic or inorganic bases are used. Triethylamine pyridine, 4-dimethylaminopyridine, sodium hydroxide, potassium hydroxide, potassium carbonate and sodium carbonate can be mentioned by way of example. Metal hydrides such as sodium hydride and calcium hydride can also be used, but only in the case of aprotic solvents.

The addition of a catalytic amount of an iodide has proven advantageous. Sodium iodide, potassium iodide, lithium iodide or tetrabutylammonium iodide can be mentioned by way of example.

The purification of the metal complexes of general formula II according to the invention is carried out by, for example, chromatography on silica gel or RP-18.

Most of the metal complexes of general formula II according to the invention can be crystallized from alcohols such as methanol, ethanol or isopropanol or else from their mixtures with water.

It has also proven advantageous to dissolve the metal complexes according to the invention in alcohols or mixtures of alcohols with water and to precipitate them by adding acetone in drops.

The drying of metal complex carboxylic acids according to the invention takes place advantageously in a vacuum at temperatures of 20°–200° C., preferably 50°–130° C., within about 6 hours to 3 days.

The metal complex carboxylic acids of general formula II that are thus obtained are stored in a moisture-free environment and can be introduced directly into a coupling reaction.

Overall, it has been possible with the metal complex carboxylic acids of general formula II according to the invention to make available important intermediate products, which make it possible to synthesize cascade polymer complexes with a small portion of by-products Examples 1 to 3 below are used to explain the synthesis of polymer complexes by means of coupling macrocyclic ligands, as described in PCT/EP 96/02671.

EXAMPLE 1 a) Bis[2-(benzyloxycarbonylamino)-ethyl]-amine 51.5 g (500 mmol) of diethylenetriamine and 139 ml (1 mol) of triethylamine are dissolved in dichloromethane and mixed at –20° C. with 161 g of benzyl cyanoformate (Fluka) in dichloromethane and then stirred overnight at room temperature. After the reaction is completed, concentration by evaporation is performed during draw-off, the residue is taken up in diethyl ether, the organic phase is washed with sodium carbonate solution and dried with sodium sulfate. The filtrate is mixed with hexane, the precipitate is filtered off and dried.

Yield: 163.4 g (88% of theory)

Elementary analysis: Cld: C 64.67 H 6.78 N 11.31 Fnd: C 64.58 H 6.83 N 11.28 b) N,N,N',N',N'',N''-Hexakis[2-(benzyloxycarbonylamino)-ethyl]-trimesic acid triamide 13.27 g (50 mmol) of trimesic acid trichloride (Aldrich) and 34.7 ml (250 mmol) of triethylamine are dissolved in dimethylformamide (DMF) and mixed at 0° C. with 65.0 g (175 mmol) of the amine described in Example 1a) and then stirred overnight at room temperature. The solution is concentrated by evaporation in a vacuum, and the residue is chromatographed on silica gel with ethyl acetate.

Yield: 39.4 g (62% of theory)

Elementary analysis: Cld: C 65.24 H 5.95 N 9.92 Fnd: C 65.54 H 5.95 N 9.87 c) $N^\alpha,N^\epsilon$-Bis (N,N'-dibenzyloxycarbonyl-lysyl)-lysine, protected "tri-lysine"

3.6 g (20 mmol) of lysine-hydrochloride and 6.95 ml (50 mmol) of triethylamine are dissolved in DMF, mixed with 26.8 g (50 mmol) of $N^\alpha,N^\epsilon$-dibenzyloxycarbonyl-lysine-p-nitrophenylester (Bachem) and stirred for 2 days at room temperature. After the reaction is completed, it is concentrated by evaporation in a vacuum, the residue is taken up in ethyl acetate and shaken out with diluted hydrochloric acid. The organic phase is dried with sodium sulfate, the solvent is concentrated by evaporation, and the residue is chromatographed with ethyl acetate/ethanol in a step gradient.

Yield: 10.7 g (57% of theory)
Elementary analysis: Cld: C 63.95 H 6.65 N 8.95 Fnd: C 63.63 H 6.69 N 8.93 d) Completely protected benzyloxycarbonyl-24mer-polyamine based on N,N,N',N',N'',N''-hexakis[2-(trilysyl-amino)-ethyl]-trimesic acid triamide 1.27 g (1 mmol) of the hexa-benzyloxycarbonylamine described in Example 1b) is dissolved in glacial acetic acid and mixed with 33% hydrogen bromide in glacial acetic acid while being stirred. After 60 minutes, the incipient precipitation is completed with diethyl ether, the hexaamine-hydrobromide produced is washed with ether, dried in a vacuum and used in the subsequent reaction described below without further purification.

Yield: 0.95 g (quantitative)

7.0 g (7.5 mmol) of the protected "tri-lysine" described in Example 1c), 1.2 g (7.5 mmol) of 1-hydroxybenzotriazole and 2.4 g (7.5 mmol) of 2-(1H-benzotriazol-1-yl)-1,1,3,3-tetramethyluronium tetrafluoroborate (TBTU; Peboc Limited, UK) are dissolved in DMF and stirred for 15 minutes. This solution is then mixed with 5.16 ml (30 mmol) of N-ethyldiisopropylamine and with 0.95 g (1 mmol) of the hexaamine-hydrobromide described above, and it is stirred overnight at room temperature. After the reaction is completed, it is concentrated by evaporation in a vacuum, and the residue is chromatographed on silica gel with ethyl acetate/ethanol (2:1).

Yield: 4.55 g (76% of theory)
Elementary analysis: Cld: C 64.35 H 6.71 N 10.52 Fnd: C 64.08 H 6.57 N 10.29 e) N-(2-Bromopropionyl)glycine-benzyl ester 55.9 g (326.1 mmol) of 2-bromopropionic acid chloride is added in drops at 0° C. to 100 g (296.4 mmol) of glycine benzyl ester-p-toluenesulfonic acid salt and 33.0 g (326.1 mmol) of triethylamine in 400 ml of methylene chloride. The temperature is not allowed to exceed 5° C. After addition is completed, it is stirred for one hour at 0° C., then for 2 hours at room temperature. 500 ml of ice water is added, and the water phase is set at pH 2 with 10% aqueous hydrochloric acid. The organic phase is separated, washed once each with 300 ml of 5% aqueous soda solution and 400 ml of water. The organic phase is dried on magnesium sulfate and evaporated to dryness in a vacuum The residue recrystallizes from diisopropyl ether.

Yield: 68.51 g (75% of theory) of a colorless, crystalline powder
Melting point: 69°–70° C.
Elementary analysis: Cld: C 48.02 H 4.70 N 4.67 Br 26.62 Fnd: C 47.91 H 4.82 N 4.51 Br 26.47 f) 1-[4-(Benzyloxycarbonyl)-l-methyl-2-oxo-3=azabutyl]-1,4,7,10-tetraazacyclododecane 50 g (162.2 mmol) of the title compound of Example 1e) is added to 55.8 g (324.4 mmol) of 1,4,7,10-tetraazacyclododecane, dissolved in 600 ml of chloroform, and it is stirred overnight at room temperature. 500 ml of water is added, the organic phase is separated and in each case washed twice with 400 ml of water. The organic phase is dried on magnesium sulfate and evaporated to dryness in a vacuum The residue is chromatographed on silica gel (mobile solvent: chloroform/methanol/aqueous 25% ammonia=10:5:1).

Yield: 40.0 g [63% of theory relative to the 1e) used] of a slightly yellowish viscous oil.
Elementary analysis: Cld: C 61.36 H 8.50 N 17.89 Fnd: C 61.54 H 8.68 N 17.68 g) 10-[4-(Benzyloxycarbonyl)-l-methyl-2-oxo-3-azabutyl]-1,4,7-tris(tert-butoxycarbonylmethyl)-1,4,7 10-tetraazacyclododecane (sodium bromide complex)

33 g (169 mmol) of bromoacetic acid-tert-butyl ester is added to 20 g (51.08 mmol) of the title compound of Example 1f) and 17.91 (169 mmol) of sodium carbonate in 300 ml of acetonitrile, and it is stirred for 24 hours at 60° C. It is cooled to 0° C., the salts are filtered out, and the filtrate is evaporated to dryness The residue is chromatographed on silica gel (mobile solvent: ethyl acetate/ethanol: 15:1). The fractions that contain the product are concentrated by evaporation, and the residue recrystallizes from diisopropyl ether.

Yield: 34.62 g (81% of theory) of a colorless, crystalline powder
Melting point: 116–117° C.
Elementary analysis Cld: C 54.54 H 7.59 N 8.37 Na 2.74 Br 9.56 Fnd: C 54.70 H 7.65 N 8.24 Na 2.60 Br 9.37 h) 10-(4—Carboxy-1-methyl-2-oxo-3-azabutyl)1,4,7-tris(tert-butoxycarbonylmethyl)-1,4,7,10-tetraazacyclododecane (sodium bromide complex)

30 g (35.85 mmol) of the title compound of Example 1g) is dissolved in 500 ml of isopropanol, and 3 g of palladium catalyst (10% Pd/C) is added. It is hydrogenated overnight at room temperature. Catalyst is filtered out, the filtrate is evaporated to dryness in a vacuum and recrystallized from acetone.

Yield: 22.75 g (85% of theory) of a colorless, crystalline powder
Melting point: 225° C. (decomposition)
Elementary analysis: Cld: C 49.86 H 7.69 N 9.38 Na 3.07 Br 10.71 Fnd: C 49.75 H 7.81 N 9.25 Na 2.94 Br 10.58 i) 24-mer N-(5-D03A-yl-4-oxo-3-azahexanoyl)-cascade polyamide based on N,N,N',N',N'',N''-hexakis[2-(trilysylamino)-ethyl]-trimesic acid triamide*)
*) D03A=1,4,7-tris(carboxymethyl)-1,4,7,10-tetraazacyclododecane 6.0 g (1 mmol) of the poly-benzyloxycarbonylamine described in Example 1d) is dissolved in glacial acetic acid and mixed with 33% hydrogen bromide in glacial acetic acid while being stirred. After 3 hours, the incipient precipitation is completed with diethyl ether, the 24-amine-hydrobromide produced is washed with ether and dried in a vacuum 35.84 g (48 mmol) of the acid described in Example 1h) above is dissolved in DMF, mixed with 7.35 g (48 mmol) of 1-hydroxybenzotriazole, with 15.41 g (48 mmol) of TBTU (Peboc Limited, UK) and with 49.3 ml (288 mmol) of N-ethyldiisopropylamine, and it is stirred for 20 minutes at room temperature. This solution is then mixed with the (1 mmol) 24-amine-hydrobromide described above, and it is stirred for 4 days at room temperature. The solution is concentrated by evaporation in a vacuum, the remaining oil is cooled in an ice bath and mixed with trifluoroacetic acid, stirred overnight at room temperature and then precipitated with diethyl ether. The precipitate is dried in a vacuum, taken up in water, set at pH 7, a YM$_3$ Amicon$^{(R)}$-ultrafiltration membrane is used to remove low-molecular portions, and the retentate is ultimately membrane-filtered and freeze-dried.

Yield: 13.5 g (683% of theory)
H$_2$O content (Karl-Fischer): 6.2%
Elementary analysis (relative to anhydrous substance): Cld: C 45.82 H 6.09 N 15.07 Na 10.79 Fnd: C 45.56 H 6.15 N 14.80 Na 10.52 k) 24-mer-Gd-complex of N-(5-D03A-yl-4-oxo-3-azahexanoyl)-cascade polyamide based on N,N,N',N',N'', N''-hexakis[2-(trilysylamino)-ethyl]-trimesic acid triamide 8.13 g (0.5 mmol) of the complexing agent acid described in Example 1i) above is set at pH 3 in water with diluted hydrochloric acid, mixed with 2.17 g (6 mmol) of Gd$_2$O$_3$g stirred for 30 minutes at 80° C., set at pH 7 after cooling and desalinated with a YM3 AMICON$^{(R)}$ ultrafiltration membrane. The retentate is ultimately membrane-filtered and freeze-dried.

Yield: 8.89 g (92.1% of theory)
$H_2O$ content (Karl-Fischer)z 9.6%
Gd determination (AAS): 19.6%
Elementary analysis (relative to anhydrous substance):
Cld: C 40.26 H 5.35 N 13.24 Gd 21.62 Fnd: C 39.98 H 5.51 N 13.42 Gd 21.37

EXAMPLE 2 a) 2-Bromopropionyl-β-alanine-benzyl ester 53.65 g (313 mmol) of 2-bromopropionic acid chloride is added in drops at 0° C. to 100 g (285 mmol) of β-alanine-benzyl ester-p-toluenesulfonic acid salt and 31.67 g (313 mmol) of triethylamine in 400 ml of methylene chloride. The temperature is not allowed to exceed 5° C. After addition is completed, it is stirred for 1 hour at 0° C., then for 2 hours at room temperature. 500 ml of ice water is added, and the water phase is set at pH 2 with 10% aqueous hydrochloric acid. The organic phase is separated, washed once each with 300 ml of 5% aqueous hydrochloric acid, 300 ml of 5% aqueous soda solution and 400 ml of water. The organic phase is dried on magnesium sulfate and evaporated to dryness in a vacuum. The residue is recrystallized from diisopropyl ethers Yield: 71.36 g (78% of theory) of a colorless, crystalline powder Elementary analysis: Cld: C 48.46 H 7.51 N 4.35 Br 24.80 Fnd: C 48.29 H 7.65 N 4.25 Br 24.61 b) 1-[5-(Benzyloxycarbonyl)-1-methyl-2-oxo-3-azapentyl]-1,4,7,10-tetraazacyclododecane 50 g (155.2 mmol) of the title compound of Example 2a) is added to 53.32 g (310 mmol) of 1,4,7,10-tetraazacyclododecane dissolved in 600 ml of chloroform, and it is stirred overnight at room temperature 500 ml of water is added, the organic phase is separated, and it is washed twice in each case with 400 ml of water. The organic phase is dried on magnesium sulfate and evaporated to dryness in a vacuum. The residue is chromatographed on silica gel (mobile solvent: chloroform/methanol/aqueous 25% ammonia: 10/5/1).

Yield: 38.39 g [61% of theory relative to the 2a) used] of a light yellowish viscous oil.

Elementary analysis Cld: C 62.20 H 8.70 N 17.27 Fnd: C 62.05 H 8.81 N 17.15 c) 10-[5-(Benzyloxycarbonyl)-1-methyl-2-oxo-3-azapentyl]-1,4,7-tris(tert-butoxycarbonylmethyl)-1,4,7,10-tetraazacyclododecane (sodium bromide complex)

31.8 g (163 mmol) of bromoacetic acid-tert-butyl ester is added to 20 g (49.32 mmol) of the title compound of Example 2b) and 17.28 g (163 mmol) of sodium carbonate in 300 ml of acetonitrile, and it is stirred for 24 hours at 60° C. It is cooled to 0° C, salts are filtered out, and the filtrate is evaporated to dryness. The residue is chromatographed on silica gel (mobile solvent- ethyl acetate/ethanol=10/1). The fractions that contain the product are concentrated by evaporation, and the residue recrystallizes from diisopropyl ether.

Yield: 31.89 g (76% of theory) of a colorless, crystalline powder

Elementary analysis: Cld: C 55.05 H 7.70 N 8.23 Na 2.69 Br 9.40 Fnd: C 55.17 H 7.85 N 8.10 Na 2.51 Br 9.30 d) 10-[5-(Carboxy)-1-methyl-2-oxo-3-azapentyl]-1,4,7-tris(tert-butoxycarbonylmethyl)-1,4,7,10-tetraazacyclododecane (sodium bromide complex)

30 g (35.26 mmol) of the title compound of Example 2c) is dissolved in 500 ml of isopropanole and 3 g of palladium catalyst (10% Pd/C) is added. It is hydrogenated overnight at room temperature. Catalyst is filtered out, the filtrate is evaporated to dryness in a vacuum and recrystallized from acetone.

Yield, 24.41 g (91% of theory) of a colorless, crystalline powder

Elementary analysis: Cld: C 50.52 H 7.82 N 9.21 Na 3.01 Br 10.52 Fnd: C 50.41 H 7.95 N 9.10 Na 2.91 Br 10.37 e) 24-mer N-(6-D03A-yl-5-oxo-4-azaheptanoyl)-cascade polyamide based on N,N,N',N',N",N"-hexakis[2-(trilysylamino)-ethyl]-trimesic acid triamide 6.0 g (1 mmol) of the poly-benzyloxycarbonylamine described in Example id) is dissolved in glacial acetic acid and mixed with 33% hydrogen bromide in glacial acetic acid while being stirred After 3 hours, the incipient precipitation is completed with diethyl ether, the 24-amine-hydrobromide produced is washed with ether and dried in a vacuum 36.52 g (48 mmol) of the acid described in Example 2d) above is dissolved in DMF, mixed with 7.35 g (48 mmol) of 1-hydroxybenzotriazole, with 15.41 g (48 mmol) of TBTU (Peboc Limited, UK) and with 49.3 ml (288 mmol) of N-ethyldiisopropylamine, and it is stirred for 20 minutes at room temperature. This solution is then mixed with the (1 mmol) 24-amine-hydrobromide described above and stirred for 4 days at room temperature The solution is concentrated by evaporation in a vacuum, the remaining oil is cooled in an ice bath and mixed with trifluoroacetic acid, stirred overnight at room temperature and then precipitated with diethyl ether. The precipitate is dried in a vacuum, taken up in water, set at pH 7, a YM3 Amicon$^{(R)}$ ultrafiltration membrane is used to remove low-molecular portions, and the retentate is ultimately membrane-filtered and freeze-dried.

Yields 14.4 g (85% of theory)
$H_2O$ content (Karl-Fischer): 8.7%
Elementary analysis (relative to anhydrous substance):
Cld: C 46.82 H 5.98 N 14.79 Na 10.59 Fnd: C 47.04 H 6.23 N 14.96 Na 10.26 f) 24-mer-Gd Complex of N-(6-D03A-yl-5-oxo-4-azaheptanoyl)-cascade polyamide based on N,N,N',N',N", N"-hexakis[2-(trilysylamino)-ethyl]-trimesic acid triamide 8.5 g (0.5 mmol) of the complexing agent acid described in Example 2,) above is set at pH 3 in water with diluted hydrochloric acid, mixed with 2.17 g (6 mmol) of $Gd_2O_3$f stirred for 30 minutes at 80° C., set at pH 7 after cooling and desalinated with a YM3 AMICON$^{(R)}$ ultrafiltration membrane. The retentate is ultimately membrane-filtered and freeze-dried.

Yield: 8.50 g (88% of theory)
$H_2O$ content (Karl-Fischer): 7.9%
Gd determination (AAS): 19.4%
Elementary analysis (relative to anhydrous substance):
Cld: C 41.12 H 5.52 N 12.99 Gd 21.21 Fnd: C 40.86 H 5.34 N 13.25 Gd 20.95

EXAMPLE 3 a) N,N'-Bis (benzyloxycarbonyl)-3-[carboxymethoxyacetyl]-3-azapentane-1,5-diamine 37.14 g (100 mmol) of the bis(benzyloxycarbonyl-aminoethyl)-amine described in Example 1a) is dissolved in DMF, mixed in an ice bath with 17.4 g (150 mmol) of diglycolic anhydride (Janssen Chimica) and 21 ml (150 mmol) of triethylamine and then stirred overnight at room temperature The solution is concentrated by evaporation in a vacuum, the residue is taken up in ethyl acetate and shaken out with diluted hydrochloric acid. The organic phase is dried with sodium sulfate and after the drying agent is filtered, it is crystallized by adding hexane.

Yield: 41.4 g (85% of theory)
Elementary analysis Cld: C 59.13 H 6.00 N 8.62 Fnd: C 58.99 H 5.93 N 8.70 b) N,N',N",N'"-Tetrakis{8-(benzyloxycarbonylamino)-6-[2-(benzyloxycarbonylaminoethyl]-5-oxo-3-oxaoctanoyl}cyclene 345 mg (2 mmol) of 1,4,7,10-tetraazacyclododecane (cyclene; Fluka) is azeotropically dehydrated with toluene. A solution of 4.88 g (10 mmol) of N,N'-bis(benzyloxycarbonyl)-3-[carboxymethoxyacetyl]-3-azapentane-1,5-diamine [Example 3a)) in tetrahydrofuran (THF) as well as 2.47 g (10 mmol) of 2-ethoxy-1-ethoxycarbonyl-1,2-dihydroquinoline (EEDQ; Fluka) are added to the cooled solution of cyclene in toluene at room temperature, and it is stirred overnight After the reaction is completed, the product is precipitated by adding hexane, decanted from solvent and reprecipitated once more from THF/hexane and then from THF/toluene. After drying in a vacuum, 2.78 g (68% of theory) of a pale yellow solid is obtained.

Elementary analysis: Cld: C 60.93 H 6.29 N 10.93 Fnd: C 60.68 H 6.40 N 10.97 c) Completely protected benzyloxycarbonyl-32-polyamine based on 32-amine condensed with $N^\alpha$, $N^\varepsilon$-bis(lysyl)-lysine ("tri-lysine") from N,N',N",N"'-tetrakis{8-benzyloxycarbonylamino)-6-(2-(benzyloxycarbonylamino)-ethyl]-5-oxo-3-oxaoctanoyl}cyclene 2.05 g (1 mmol) of the octa-benzyloxycarbonylamine described in Example 3b) is dissolved in glacial acetic acid and mixed with 33% hydrogen bromide in glacial acetic acid while being stirred. After 90 minutes, the incipient precipitation is completed with diethyl ether, the octa-amine-hydrobromide produced is washed with ether, dried in a vacuum and used in the subsequent reaction described below without further purification.

Yield: 1.6 g (quantitative)

9.4 g (10 mmol) of the protected "tri-lysine" described in Example 1c), 1.5 g (10 mmol) of 1-hydroxybenzotriazole and 3.2 g (10 mmol) of 2-(1H-benzotriazol-1-yl)-1,1,3,3-tetramethyluronium tetrafluoroborate (TBTU; Peboc Limited, UK) are dissolved in DMF and stirred for 15 minutes. This solution is then mixed with 5.16 ml (30 mmol) of N-ethyldiisopropylamine and with 1.6 g (1 xmol) of the octaamine-hydrobromide described above, and it is stirred overnight at room temperature. After the reaction is completed, it is concentrated by evaporation in a vacuum, and the residue is chromatographed on silica gel with dichloromethane/ methanol (10:1).

Yield: 6.0 g (72% of theory)

Elementary analysis: Cld: C 63.32 H 6.76 N 10.74 Fnd: C 62.98 H 6.91 N 10.43 d) 32-mer N-(5-D03A-yl-4-oxo-3-azahexanoyl)-cascade polyamide based on the 32-mer amine described in Example 3c) above 8.35 g (1 mmol) of the 32-mer-benzyloxycarbonylamine described in Example 3c) is dissolved in glacial acetic acid and mixed with 33% hydrogen bromide in glacial acetic acid while being stirred. After 3 hours, the incipient precipitation is completed with diethyl ether; the 32-amine-hydrobromide produced is washed with ether and dried in a vacuum.

47.8 g (64 mmol) of the acid described in Example 1h) is dissolved in DMF, mixed with 9.8 g (64 mmol) of 1-hydroxybenzotriazole, with 20.5 g (64 mmol) of TBTU (Peboc Limited, UK) and with 65.7 ml (384 mmol) of N-ethyldiisopropylamine, and it is stirred for 20 minutes at room temperature. This solution is then mixed with the (1 mmol) 32-amine-hydrobromide described above and stirred for 4 days at room temperature. The solution is concentrated by evaporation in a vacuum, the remaining oil is cooled in an ice bath and mixed with trifluoroacetic acid, stirred overnight at room temperature and then precipitated with diethyl ether. The precipitate is dried in a vacuum, taken up in water, set at pH 7, a YM3 Amicon$^{(R)}$ ultrafiltration membrane is used to remove low-molecular portions, and the retentate is ultimately membrane-filtered and freeze-dried.

Yield: 17.2 g (76.4% of theory)

$H_2O$ content (Karl-Fischer): 7.6%

Elementary analysis (relative to anhydrous substance): Cld: C 45.73 H 6.12 N 15.08 Na 10.61 Fnd: C 45.89 H 6.30 N 14.84 Na 10.31 e) 32-mer-Gd Complex of N-(5-D03A-yl-4-oxo-3-azahexanoyl)-cascade polyamide based on the 32-mer amine described in Example 3c)

10.4 g (0.5 mmol) of the complexing agent acid described in Example 3d) above is set at pH 3 in water with diluted hydrochloric acid, mixed with 2q89 g (8 mmol) of $Gd_2O_3$, stirred for 30 minutes at 80° C., set at pH 7 after cooling and desalinated with a YM3 AMICON$^{(R)}$ ultrafiltration membrane. The retentate is ultimately membrane-filtered and freeze-dried.

Yield: 12.1 g (91.1% of theory)

$H_2O$ content (Karl-Fischer): 11.0%

Gd determination (AAS): 18.6%

Elementary analysis (relative to anhydrous substance): Cld: C 40.26 H 5.39 N 13.28 Gd 21.30 Fnd: C 40.10 H 5.21 N 13.04 Gd 21.03

The ytterbium complex is obtained analogously with $Yb_2(CO_3)_3$:

Elementary analysis (relative to anhydrous substance): Cld: C 39.42 H 5.28 N 13.00 Yb 22.94 Fnd: C 39.29 H 5.40 N 12.81 Yb 22.65

Examples 4 to 14 below are used to explain the object of the invention:

EXAMPLE 4 a) 10-[4—Carboxy-1-methyl-2-oxo-3-azabutyl)-1,4,7,10-tetraazacyclododecane-1,4,7-triacetic acid 77 g (103.1 mmol) of the title compound of Example 1h is dissolved in 500 ml of trifluoroacetic acid and stirred for 3 hours at room temperature. It is evaporated to dryness, the residue is taken up in 300 ml of water and the solution is added to a column, filled with Reillex$^{(R)}$ 425 PVP. It is eluted with water. The product-containing fractions are combined and evaporated to dryness, and the residue is recrystallized from methanol/acetone.

Yield: 44.04 g (84% of theory) of a colorless, hygroscopic solid

Water content: 6.5%

Elementary analysis (relative to anhydrous substance) Cld: C 47.99 H 6.99 N 14.73 Fnd: C 47.83 H 7.12 N 14.55 b) Gadolinium complex of 10-(4-carboxy-1-methyl-2-oxo-3-azabutyl]-1,4,7,10-tetraazacyclododecane-1,4,7-triacetic acid 15.27 g (42.06 mmol) of gadolinium oxide is added to 40 g (84.12 mmol) of the title compound of Example 4a, dissolved in 400 ml of water, and it is heated for 3 hours to 90° C. It is evaporated to dryness (vacuum), and the residue is recrystallized from 90% aqueous ethanol. The crystals are suctioned off, washed once with ethanol, then with acetone and finally with diethyl ether and dried in a vacuum furnace at 130° C. (24 hours).

Yield: 50.53 g (93% of theory) of a colorless, crystalline powder

Water content: 2.5%

Elementary analysis (relative to anhydrous substance): Cld: C 36.24 H 4.80 N 11.12 Gd 24.97 Fnd: C 36.35 H 4.95 N 10.98 Gd 24.80

EXAMPLE 5

Dysprosium complex of 10-[4-carboxy-1-methyl-2-oxo-3-azabutyl)-1,4,7,10-tetraazacyclododecane-1,4,7-triacetic acid 7.84 g (21.03 mmol) of dysprosium oxide is added to 20 g (42.06 mmol) of the title compound of Example 4a, dissolved in 200 ml of water, and it is heated for 3 hours to 90° C. It is evaporated to dryness (vacuum) and the residue is recrystallized from 90% aqueous ethanol The crystals are suctioned off , washed once with ethanol, then with acetone and finally with diethyl ether and dried in a vacuum furnace at 130° C. (24 hours)

Yield: 24.98 (91% of theory) of a colorless, crystalline powder

Water content: 2.7%

Elementary analysis (relative to anhydrous substance) Cld: C 35.94 H 4.76 N 11.03 Dy 25.59 Fnd: C 35.85 H 4.91 N 10.90 Dy 25.42

EXAMPLE 6

Ytterbium complex of 10-(4-carboxy-1-methyl-2-oxo-3-azabutyl]-1,4,7,10-tetraazacyclododecane-1,4,7-triacetic acid 8.29 g (21.03 mmol) of ytterbium oxide is added to 20 g (42.06 mmol) of the title compound of Example 4a, dissolved in 200 ml of water, and it is heated for 3 days to 90° C. It is evaporated to dryness (vacuum) , and the residue is recrystallized from 90% aqueous ethanol The crystals are suctioned off e washed once with ethanol, then with acetone and finally with diethyl ether and dried in a vacuum furnace at 130° C. (24 hours)

Yield: 21.79 (78% of theory) of a colorless, crystalline powder

Water content, 2.8%

Elementary analysis (relative to anhydrous substances Cld: C 35.35 H 4.68 N 10.85 Yb 26.81 Fnd: C 35.25 H 4.79 N 10.68 Yb 26.61 a) N-(2-Bromobutyryl)-glycine benzyl ester 65.96 g (355.7 mmol) of α-bromobutyric acid chloride is added in drops at 0° C. to 100 g (296.4 mmol) of glycine benzyl ester p-toluenesulfonic acid salt and 89.98 g (889.2 mmol) of triethylamine in 500 ml of methylene chloride. In this case, the temperature remains between 0° C.–5° C. 1000 ml of 5% aqueous hydrochloric acid is added, and the organic phase is separated. The organic phase is extracted once more with 500 ml of 5% aqueous hydrochloric acid, dried on magnesium sulfate and evaporated to dryness in a vacuum. The residue is recrystallized from diisopropyl ether.

Yield: 75.43 g (81% of theory) of a colorless, crystalline powder

Elementary analysis: Cld: C 49.70 H 5.13 N 4.46 Br 25.43 Fnd: C 49.51 H 5.27 N 4.31 Br 25.28 b ) 10-[4- (Benzyloxycarbonyl) -1-ethyl-2-oxo- 3-azabutyl]-1,4,7,10-tetraazacyclododecane-1,4,7-triacetic acid-tri-tert-butyl ester 500 ml of acetonitrile is added to 50 g (159.14 mmol) of the title compound of Example 7a, 36.98 g (79.6 mmol) of 1,4,7-tris(tert-butoxy-carbonylmethyl)-1,4,7,10-tetraazacyclododecane (=D03A-tri-tert-butyl ester), 44 g (318.4 mmol) of potassium carbonate and 1 g (60 mmol) of potassium iodide, and it is refluxed for 12 hours. Salts are filtered out, and the filtrate is evaporated to dryness in a vacuum. The residue is dissolved in 80. ml of dichloromethane and extracted twice with 300 ml of 5% aqueous sodium carbonate solution each. The organic phase is dried on magnesium sulfate and concentrated by evaporation. After chromatography on silica gel (mobile solvent: dichloromethane/methanol=20.:1), 19.11 g of the title compound (32.1% of theory) is obtained as a colorless foam.

Elementary analysis: Cld: C 62.63 H 8.76 N 9.36 Fnd: C 62.51 H 8.91 N 9.18 c) 10-(4—Carboxy-1-ethyl-2-oxo-3-azabutyl)-1,4,7,10-tetraazacyclododecane-1,4,7-triacetic acid-tri-tert-butyl ester 19 g (25.40 mmol) of the title compound of Example 7b is dissolved in 300 ml of isopropanol, and 2 g of palladium catalyst (10% Pd/C) is added. It is hydrogenated overnight at room temperature. Catalyst is filtered out, and the filtrate is evaporated to dryness.

Yield: 16.54 g (99% of theory) of a viscous oil

Elementary analysis: Cld: C 58.43 H 9.04 N 10.65 Fnd: C 58.65 H 9.27 N 10.47 d) 10-(4—Carboxy-1-ethyl-2-oxo-3-azabutyl)-1,4,7,10-tetraazacyclododecane-1,4,7-triacetic acid 16 g (24.32 mmol) of the title compound of Example 7c is dissolved in 100 ml of trifluoroacetic acid, and it is stirred for 3 hours at room temperature. It is evaporated to dryness, the residue is taken up in 50 ml of water, and the solution is added to a column, filled with Reillex $^{(R)}$ 425 PVP. It is eluted with water. The product-containing fractions are combined and evaporated to dryness, and the residue is recrystallized from methanol/acetone.

Yield: 10.10 g (79% of theory) of a colorless, hygroscopic solid

Water content: 6.9%

Elementary analysis (relative to anhydrous substance): Cld: C 49.07 H 7211 N 14.31 Fnd: C 49.28 H 7.39 N 14.15 e) Gadolinium complex of 10-(4-carboxy-1-ethyl-2-oxo-3-azabutyl)-1,4,7,10-tetraazacyclododecane-1,4,7-triacetic acid 3.33 g (9.19 mmol) of gadolinium oxide is added to 9 g (18.38 mmol) of the title compound of Example 7d, dissolved in 70 ml of water, and it is heated for 3 hours to 90° C. It is evaporated to dryness (vacuum), and the residue is recrystallized from 90% aqueous ethanol. The crystals are suctioned off, washed once with ethanol, then with acetone and finally with diethyl ether and dried in a vacuum furnace at 130° C. (24 hours).

Yield: 11.44 g (94% of theory) of a colorless, crystalline powder

Water content: 2.8%

Elementary analysis (relative to anhydrous substance: Cld: C 37.32 H 5.01 N 10.88 Gd 24.43 Fnd: C 37.15 H 5.21 N 10.65 Gd 24.25

EXAMPLE 8

Dysprosium complex of 10-(4-carboxy-1-ethyl-2-oxo-3-azabutyl)-1,4,7,10-tetraazacyclododecane-1,4,7-triacetic acid 3.81 g (10.21 mmol) of dysprosium oxide is added to 10 g (20.43 mmol) of the title compound of Example 7d, dissolved in 80 ml of water, and it is heated for 3 hours to 90° C. It is evaporated to dryness (vacuum), and the residue is recrystallized from 90% aqueous ethanol. The crystals are suctioned off, washed once with ethanol, then with acetone and finally with diethyl ether, and it is dried in a vacuum furnace at 130° C. (24 hours).

Yield: 12.40 g (91% of theory) of a colorless, crystalline powder

Water content: 2.7%

Elementary analysis (relative to anhydrous substance): Cld: C 37.01 H 4.97 N 10.79 Dy 25.04 Fnd: C 36.85 H 5.13 N 10.61 Dy 24.87 a) N-[2-Bromo-2-phenyl-acetyl]-glycolic acid-tert-butyl ester 72.69 g (311.3 mmol) of α-bromophenylacetic acid chloride is added in drops at 0° C. to 50 g (296.5 mmol) of glycine-tert-butyl ester hydrochloride salt and 90 g (889.5 mmol) of triethylamine in 500 ml of methylene chloride. In this case, the temperature remains between 0° C.–5° C. 1000 ml of 5% aqueous hydrochloric acid is added, and the organic phase is separated. The organic phase is extracted once more with 500 ml of 5% aqueous hydrochloric acid, dried on magnesium sulfate and evaporated to dryness in a vacuum. The residue is recrystallized from diisopropyl ether/n-hexane.

Yield: 78.8 g (81% of theory)

Elementary analysis: Cld: C 51.23 H 5.53 N 4.27 Br 24.35 Fnd: C 51.15 H 5.66 N 4.11 Br 24 18 b) 1-[4-(tert-Butoxycarbonyl)-oxo-1-phenyl-3-azabutyl]-4,7,10-tris (tert-butoxycarbonylmethyl)-1,4,7,10-tetraazacyclododecane 500 ml of acetonitrile is added to 50 g (159.14 mmol) of the title compound of Example 9a, 53.12 g (114.3 mmol) of 1,4,7-tris(tert-butoxy-carboxymethyl)-1,4,7,10-tetraazacyclododecane (=D03A-tri-tert-butyl ester), 63,16 g (457.0 mmol) of potassium carbonate and 1 g (6 mmol) of potassium iodide, and it is refluxed for 12 hours. Salts are filtered out, and the filtrate is evaporated to dryness in a vacuum. The residue is dissolved in 1000 ml of dichloromethane, and it is extracted twice with 400 ml of 5% aqueous sodium carbonate solution each. The combined organic phases are dried on magnesium sulfate and concentrated by evaporation. After chromatography on silica gel (mobile solvent: dichloromethane/methanol=20:1), 27 g of the title compound (31% of theory) is obtained as a colorless foam.

Elementary analysis: Cld: C 63.05 H 8.86 N 9.19 Fnd: C 62.91 H 8.98 N 9.02 c) 1-(4—Carboxy-2-oxo-1-phenyl-3-azabutyl)-4,7,10-tris (carboxymethyl)-1,4,7,10-tetraazacyclododecane 26 g (34.12 mmol) of the title compound of Example 9b is dissolved in 300 ml of trifluoroacetic acid, and it is stirred for 3 hours at room temperature. It is evaporated to dryness, the residue is taken up in 80 ml of water, and the solution is added to a column, filled with Reillex$^{(R)}$ 425 PVP. It is eluted with water. The product-containing fractions are combined and evaporated to dryness, and the residue is recrystallized from methanol/acetone.

Yield: 16.22 g (81% of theory) of a colorless, hygroscopic solid

Water content: 8.4%

Elementary analysis (relative to anhydrous substance): Cld: C 53.62 H 6.56 N 13.03 Fnd: C 53.48 H 6.71 N 12.87 d) Gadolinium complex of l-(4-carboxy-2-oxo-1-phenyl-3-azabutyl)-4,7,10-tris(carboxymethyl)-1,4,7,10-tetraazacyclododecane 5.06 g (13.95 mmol) of gadolinium oxide is added to 15 g (27.90 mmol) of the title compound of Example 9c, dissolved in 200 ml of water, and it is heated for 3 hours to 90° C. It is evaporated to dryness (vacuum), and the residue is recrystallized from 90% aqueous ethanol. The crystals are suctioned off, washed once with ethanol, then with acetone and finally with diethyl ether, and it is dried in a vacuum furnace at 130° C. (24 hours)

Yield: 18.27 g (92% of theory) of a colorless, crystalline powder

Water content: 2.8%

Elementary analysis (relative to anhydrous substance): Cld: C 41.67 H 4.66 N 10.12 Gd 22.73 Fnd: C 41.40 H 4.80 N 9.95 Gd 22.51

EXAMPLE 10 a) N-(2-Bromopropionyl)-β-alanine 72.69 g (311.3 mmol) of a-bromopropionic acid chloride is added in drops at 0° C. to 40 g (448.98 mmol) of b-alanine and 90 g (889.5 mmol) of triethylamine in 500 ml of methylene chloride. In this case, the temperature remains between 0° C.–5° C. 1000 ml of 5% aqueous hydrochloric acid is added, and the organic phase is separated. The organic phase is extracted once more with 500 ml of 5% aqueous hydrochloric acid, dried on magnesium sulfate and evaporated to dryness in a vacuum. The residue is recrystallized from acetone/diisopropyl ether.

Yield: 62.37 g (62% of theory)

Elementary analysis: Cld: C 32.16 H 4.50 N 6.25 Br 35.66 Fnd: C 32.02 H 4.65 N 6.13 Br 35.74 b) 10-(5-Carboxy-1-methyl-2-oxo-3-azapentyl)-1,4,7,10-tetraazacyclododecane-1,4,7-triacetic acid 46.38 g (133.9 mmol) of 1,4,7-tris(carboxymethyl)-1,4,7,10-tetraazacyclododecane (=D03A), 129.54 g (937.3 mmol) of potassium carbonate and 1 g (6 mmol) of potassium iodide are added to 60 g (267.80 mmol) of the title compound of Example 10a, dissolved in 300 ml of acetonitrile/200 ml of water. It is refluxed for 12 hours. It is evaporated to dryness in a vacuum, the residue is taken up in 500 ml of methanol, and then salts are filtered out. The filtrate is evaporated to dryness, the residue is taken up in 300 ml of water and set at pH 1 with 5N hydrochloric acid. Then purification is done on a column filled with Reillex$^{(R)}$ 425 PVP. It is eluted with water. The product-containing fractions are evaporated to dryness in a vacuum, and the residue is recrystallized from methanol/acetone.

Yield: 19.19 g (27% of theory) of a colorless solid

Water content: 7.8%

Elementary analysis (relative to anhydrous substance): Cld: C 49.07 H 7.21 N 14.31 End: C 48.85 H 7.31 N 14.19 c) Gadolinium complex of 10-(5-carboxy-1-methyl-2-oxo-3-azapentyl)-1,4,7,10-tetraazacyclododecane-1,4,7-triacetic acid 6.66 g (18.38 mmol) of gadolinium oxide is added to 18 g (36.77 mmol) of the title compound of Example 10b, dissolved in 300 ml of water, and it is heated for 3 hours to 90° C. It is evaporated to dryness (vacuum), and the residue is recrystallized from 90% aqueous ethanol. The crystals are suctioned off, washed once with ethanol, then with acetone and finally with diethyl ether and dried in a vacuum furnace at 130° C. (24 hours).

Yield: 21.6 g (89% of theory) of a colorless, crystalline powder

Water content: 2.5%

Elementary analysis (relative to anhydrous substance): Cld: C 37.32 H 5.01 N 10.88 Gd 24.43 Fnd: C 37.15 H 5.21 N 10.67 Gd 24.25

EXAMPLE 11 a) N (2-Bromopropionyl)-11-aminoundecanoic acid 30.65 g (178.8 mmol) of α-bromopropionic acid chloride is added in drops at 0° C. to 30 g (149 mmol) of 11-aminoundecanoic acid and 45.24 g (447.1 mmol) of triethylamine in 600 ml of methylene chloride. In this case, the temperature remains between 0° C.–5° C. 800 ml of 5% aqueous hydrochloric acid is added, and the organic phase is separated. The organic phase is extracted once more with 300 ml of 5% aqueous hydrochloric acid, dried on magnesium sulfate and evaporated to dryness in a vacuum. The residue is recrystallized from acetone/diisopropyl ether.

Yield: 25.55 g (51% of theory)

Elementary analysis: Cld: C 50.01 H 7.79 N 4.17 Br 23.76 Fnd: C 49.82 H 7.95 N 4.03 Br 23.59 b) 10-(13—Carboxy-1-methyl-2-oxo-3-aza-tridecyl)-1,4,7,10-tetraazacyclododecane-1,4,7-triacetic acid 12.88 g (37.18 mmol) of 1,4,7-triscarboxymethyl-1,4,7,10-tetraazacyclododecane (=D03A), 35.97 g (260.3 mmol)

of potassium carbonate and 1 g (6 mmol) of potassium iodide are added to 25 g (74.35 mmol) of the title compound of Example 11a, dissolved in 250 ml of acetonitrile/150 ml of water. It is refluxed for 12 hours. It is evaporated to dryness in a vacuum, the residue is taken up in 300 ml of methanol, and then salts are filtered out. The filtrate is evaporated to dryness, the residue is taken up in 300 ml of water, and it is set at pH 1 with 5N hydrochloric acid. Then purification is done on a column filled with Reillex$^{(R)}$ 425 PVP. It is eluted with water. The product-containing fractions are evaporated to dryness in a vacuum, and the residue is recrystallized from methanol/acetone.

Yield: 6.63 g (27% of theory) of a colorless solid

Water content: 8.9%

Elementary analysis (relative to anhydrous substance): Cld: C 55.89 H 8.54 N 11.64 Fnd: C 55.71 H 8.70 N 11.57 c) Gadolinium complex of 10-(13-carboxy-1-methyl-2-oxo-3-aza-tridecyl)-1,4,7,10-tetraazacyclododecane-1,4,7-triacetic acid 1.81 g (10.21 mmol) of gadolinium oxide is added to 6 g (9.97 mmol) of the title compound of Example 11b, dissolved in 80 ml of water, and it is heated for 3 hours to 90° C. It is evaporated to dryness (vacuum) and the residue is recrystallized from 90% aqueous 2-propanol. The crystals are suctioned off, washed once with ethanol, then with acetone and finally with diethyl ether and dried in a vacuum furnace at 130° C. (24 hours).

Yield: 6.75 g (87% of theory) of a colorless crystalline powder

Water content: 2.9%

Elementary analysis (relative to anhydrous substance): Cld: C 44.49 H 6.40 N 9.26 Gd 20.80 Fnd: C 44.28 H 6.55 N 9.11 Gd 20.63

EXAMPLE 12 a) N-(2-Bromopropionyl)-alanine 69.26 g (404 mmol) of α-bromopropionic acid chloride is added in drops at 0° C. to 30 g (336.7 mmol) of alanine and 102.2 g (1010.2 mmol) of triethylamine in 600 ml of methylene chloride. In this case, the temperature remains between 0° C.–5° C. 1000 ml of 5% aqueous hydrochloric acid is added, and the organic phase is separated. The organic phase is extracted once more with 400 ml of 5% aqueous hydrochloric acid, dried on magnesium sulfate and evaporated to dryness in a vacuum. The residue is recrystallized from acetone/diisopropyl ether.

Yield: 52.05 g (69% of theory)

Elementary analysis (relative to anhydrous substance): Cld: C 32.16 H 4.50 N 6.25 Br 35.66 Fnd: C 32.33 H 4.70 N 6.13 Br 35.41 b) 10-(4—Carboxy-1-methyl-2-oxo-3-azapentyl)-1,4,7,10-tetraazacyclododecane-1,4,7-triacetic acid 38.65 g (111.6 mmol) of 1,4,7-triscarboxymethyl-1,4,7,10-tetraazacyclododecane (=D03A), 108 g (781.2 mmol) of potassium carbonate and 1 g (6 mmol) of potassium iodide are added to 50 g (223.2 mmol) of the title compound of Example 12a, dissolved in 300 ml of acetonitrile/200 ml of water. It is refluxed for 12 hours. It is evaporated to dryness in a vacuum, the residue is taken up in 500 ml of methanol, and then salts are filtered out. The filtrate is evaporated to dryness, the residue is taken up in 300 ml of water and set at pH 1 with 5N hydrochloric acid. Then purification is done on a column filled with Reillex$^{(R)}$ 425 PVP. It is eluted with water. The product-containing fractions are evaporated to dryness in a vacuum, and the residue is recrystallized from methanol/acetone.

Yield: 17.72 g (30% of theory) of a colorless solid

Water content: 7.5%

Elementary analysis (relative to anhydrous substance): Cld: C 49.07 H 7.21 N 14.31 Fnd: C 49.23 H 7.38 N 14.15 c) Gadolinium complex of 10-(4-carboxy-1-methyl-2-oxo-3-azapentyl)-1,4,7,10-tetraazacyclododecane-1,4,7-triacetic acid 5.55 g (15.32 mmol) of gadolinium oxide is added to 15 g (30.64 mmol) of the title compound of Example 12b, dissolved in 150 ml of water, and it is heated for 3 hours to 90° C. It is evaporated to dryness (vacuum), and the residue is recrystallized from 90% aqueous ethanol. The crystals are suctioned off, washed once with ethanol, then with acetone and finally with diethyl ether and dried in a vacuum furnace at 130° C. (24 hours).

Yield: 18.22 g (90% of theory) of a colorless, crystalline powder

Water content: 2.6%

Elementary analysis (relative to anhydrous substance): Cld: C 37.32 H 5.01 N 10.88 Gd 24.43 Fnd: C 37.13 H 5.20 N 10.61 Gd 24.41

EXAMPLE 13 a) N-(2-Bromopropionyl)-valine 70.2 g (409.7 mmol) of a-bromopropionic acid chloride is added in drops at 0° C. to 40 g (341.4 mmol) of valine and 103.7 g (1024 mmol) of triethylamine in 600 ml of methylene chloride. In this case, the temperature remains between 0° C.–5° C. 1000 ml of 5% aqueous hydrochloric acid is added, and the organic phase is separated. The organic phase is extracted once more with 500 ml of 5% aqueous hydrochloric acid, dried on magnesium sulfate and evaporated to dryness in a vacuum The residue is recrystallized from acetone/diisopropyl ether.

Yield: 59.39 g (69% of theory)

Elementary analysis (relative to anhydrous substance): Cld: C 38.11 H 5.60 N 5.56 Br 31.69 Fnd: C 38.01 H 5.75 N 5.41 Br 31.48 b) 10-(4—Carboxy-1,5-dimethyl-2-oxo-3-azahexyl)-1,4,7,10-tetraazacyclododecane-1,4,7-triacetic acid 37.8 g (109.7 mmol) of 1,4,7-triscarboxymethyl-1,4,7,10-tetraazacyclododecane (=D03A), 106.13 g (767.9 mmol) of potassium carbonate and 1 g (6 mmol) of potassium iodide are added to 55 g (218.2 mmol) of the title compound of Example 13a, dissolved in 200 ml of acetonitrile/200 ml of water. It is refluxed for 12 hours. It is evaporated to dryness in a vacuum, the residue is taken up in 500 ml of methanol, and then salts are filtered out. The filtrate is evaporated to dryness, and the residue is taken up in 300 ml of water and set at pH 1 with 5N hydrochloric acid. Then purification is done on a column filled with Reillex$^{(R)}$ 425 PVP. It is eluted with water. The product-containing fractions are evaporated to dryness in a vacuum, and the residue is recrystallized from methanol/acetone Yield: 17.57 g (29% of theory) of a colorless solid Water content: 6.3%

Elementary analysis (relative to anhydrous substance): Cld: C 51.05 H 7.59 N 13.53 Fnd: C 51.18 H 7.70 N 13.39 c) Gadolinium complex of 10-(4-carboxy-1,5-dimethyl-2-oxo-3-azahexyl]-1,4,7,10-tetraazacyclododecane-1,4,7-triacetic acid 5.25 g (14.49 mmol) of gadolinium oxide is added to 15 g (28.98 mmol) of the title compound of Example 13b, dissolved in 150 ml of water, and it is heated for 3 hours to 90° C. It is evaporated to dryness (vacuum), and the residue is recrystallized from 90% aqueous ethanol. The crystals are suctioned off, washed once with ethanol, then with acetone and finally with diethyl ether and dried in a vacuum furnace at 130° C. (24 hours).

Yield: 18.57 g (93% of theory) of a colorless, crystalline powder

Water content: 2.5%

Elementary analysis (relative to anhydrous substance):
Cld: C 39.33 H 5.40 N 10.42 Gd 23.41 Fnd: C 39.17 H 5.55 N 10.31 Gd 23.27

EXAMPLE 14 a) N-(2-Bromoacetyl)-glycine-tert-butyl ester 77.8 g (385.5 mmol) of α-bromoacetic acid bromide is added in drops at 0° C. to 50 g (296.5 mmol) of glycine-tert-butyl ester hydrochloride salt and 90 g (889.5 mmol) of triethylamine in 500 ml of methylene chloride. In this cases the temperature remains between 0° C.–5° C. 1000 ml of 5% aqueous hydrochloric acid is added, and the organic phase is separated. The organic phase is extracted once more with 500 ml of 5% aqueous hydrochloric acid, dried on magnesium sulfate and evaporated to dryness in a vacuum The residue is recrystallized from diisopropyl ether/n-hexane.

Yield: 30.5 g (61% of theory)

Elementary analysis: Cld: C 38.11 H 5.60 N 5.65 Br 31.69 Fnd: C 37.92 H 5.76 N 5.38 Br 31.42 b) 10-[4-(tert-Butoxycarbonyl)-2-oxo-3-azabutyl]-1,4,7,10-tetraazacyclododecane-1,4,7-triacetic acid-tri-tert-butyl ester 200 ml of acetonitrile is added to 20.35 g (80.70 mmol) of the title compound of Example 14a, 25 g (53.8 mmol) of 1,4,7-tris(tert-butoxy-carboxymethyl)-1,4,7,10-tetraazacyclododecane (=D03A-tri-tert-butyl ester), 29.74 g (215.8 mmol) of potassium carbonate and 1 g (6 mmol) of potassium iodide, and it is refluxed for 12 hours. Salts are filtered out, and the filtrate is evaporated to dryness in a vacuum The residue is dissolved in 800 ml of dichloromethane and extracted twice with 200 ml of 5% aqueous sodium carbonate solution. The organic phase is dried on magnesium sulfate and concentrated by evaporation. After chromatography on silica gel (mobile solvent: dichloromethane/methanol=20:1), 25.09 g of the title compound (68% of theory) is obtained as a colorless foam.

Elementary analysis: Cld: C 59.54 H 9.26 N 10.21 Fnd: C 59.38 H 9.42 N 10.03 c) 10-[4—Carboxy-2-oxo-3-azabutyl]-1,4,7,10-tetraazacyclododecane-1,4,7-triacetic acid 25 g (36.45 mmol) of the title compound of Example 14b is dissolved in 300 ml of trifluoroacetic acid, and it is stirred for 3 hours at room temperature. It is evaporated to dryness, the residue is taken up in 80 ml of water, and the solution is added to a column, filled with Reillex$^{(R)}$ 425 PVP. It is eluted with water. The product-containing fractions are combined and evaporated to dryness, and the residue is recrystallized from methanol/acetone.

Yield: 15.24 g (84% of theory) of a colorless, hygroscopic solid

Water content: 7.3%

Elementary analysis (relative to anhydrous substance):
Cld: C 46.85 H 6.77 N 15.18 Fnd: C 46.61 H 6.95 N 15.02 d) Gadolinium complex of 10-[4-carboxy-2-oxo-3-azabutyl]-1,4,7,10-tetraazacyclododecane-1,4,7-triacetic acid 5.86 g (16.25 mmol) of gadolinium oxide is added to 15 g (32.50 mmol) of the title compound of Example 14c, dissolved in 200 ml of water, and it is heated for 3 hours to 90° C. It is evaporated to dryness (vacuum), and the residue is recrystallized from 90% aqueous ethanol. The crystals are suctioned off washed once with ethanol, then with acetone and finally with diethyl ether and dried in a vacuum furnace at 130° C. (24 hours).

Yield: 18.92 g (92% of theory) of a colorless, crystalline powder

Water content: 2.7%

Elementary analysis (relative to anhydrous substance):
Cld: C 35.11 H 4.58 N 11.37 Gd 25.54 Fnd: C 34.92 H 4.71 N 11.14 Gd 25.33

The examples below are used to explain the use of the macrocyclic metal complex carboxylic acids according to the invention:

EXAMPLE 15

24-mer-Gd Complex of N-(5-D03A-yl-4-oxo-3-azahexanoyl)-cascade polyamide based on N,N,N',N',N'', N''-hexakis[2-(trilysylamino)-ethyl]-trimesic acid triamide 4.2 g (0.7 mmol) of the benzyloxycarbonyl-24mer-polyamine based on N,N,N',N',N'',N''-hexakis[2-(trilysylamino)-ethyl]-trimesic acid triamide, described in Example 1d, is dissolved in glacial acetic acid and mixed with 33% hydrogen bromide in glacial acetic acid while being stirred. After 3 hours, the incipient precipitation is completed with diethyl ether, the 24mer-amine-hydrobromide produced is washed with ether, dried in a vacuum (3.3 g, quantitative) and used in the following reaction without further purification.

31.74 g (50.4 mmol, 3X excess) of the Gd-complex of 10-[4-carboxy-1-methyl-2-oxo-3-azabutyl]-1,4,7,10-tetraazacyclododecane-1,4,7-triacetic acid described in Example 4b is dissolved in 250 ml of formamide under heat After cooling to room temperature, 13.69 g (55.4 mmol) of 2-ethoxy-1-ethoxycarbonyl-1,2-dihydroquinoline (EEDQ, Fluka), 3.3 g (0.7 mmol) of the above-described tetracosahydrobromide and 1.70 g (16.8 mmol) of triethylamine are added, and it is stirred overnight at room temperature The solution is then mixed with acetone,, the precipitate is suctioned off, dried, taken up in water, insoluble portions are filtered out, and the filtrate is desalinated with an Amicon$^{(R)}$ YM3 ultrafiltration membrane (cut off 3,000 Da) and low-molecular components are removed. The retentate is then freeze-dried Yield: 10.46 g (78% of theory)

$H_2O$ content (Karl Fischer): 9%

Gd determination (AAS): 18.8%

Elementary analysis (relative to anhydrous substance):
Cld: C 40.26 H 5.35 N 13.24 Gd 21.62 Fnd: C 40.07 H 5.32 N 13.14 Gd 21.43

The MALDI-MS (Matrix Assisted Laser Desorption/Ionization Mass Spectrometry: e.g.: F. Hillenkamp, M. Karas, R. Beavis, B. T. Chait, Anal. Chem. 63, 1193A (1991)) shows signals at m/z=about 17,470 (24mer), about 16,960 (23mer) and about 16,480 (22mer) and thus confirms less by-product dispersion than the product that is obtained according to Example 1k, which has the following dispersion: Signals at m/z=about 17,450 (24mer), about 16,830 (23mer), about 16,230 (22mer), about 15,680 (21mer), about 15070 (20mer) and 14,450 (19mer).

EXAMPLE 16

24mer-Gd-complex of N-(6-D03A-yl-5-oxo-4-azaheptanoyl) -cascade polyamide based on N,N,N',N',N'', N''-hexakis[2-(trilysylamino)-ethyl]-trimesic acid triamide 4.2 g (0.7 mmol) of the completely protected benzyloxycarbonyl-24mer-polyamine based on N,N,N',N', N'',N''- hexakis[2-(trilysylamino)-ethyl]-trimesic acid triamide described in Example id is dissolved in glacial acetic acid and mixed with 33% hydrogen bromide in glacial acetic acid while being stirred. After 3 hours, the incipient precipitation is completed with diethyl ether, the 24mer-amine-hydrobromide produced is washed with ether, dried in a vacuum (3.3 g, quantitative) and used in the following reaction without further purification.

32.45 g (50.4 mmol, 3X excess) of the Gd complex of 10-(5-carboxy-1-methyl-2-oxo-3-aza-pentyl)-1,4,7,10-tetraazacyclododecane-1,4,7-triacetic acid described in Example 10c is dissolved in 250 ml of formamide under heat. After cooling to room temperature, 13.69 g (55.4 mmol) of 2-ethoxy-1-ethoxycarbonyl-1,2-dihydroquinoline (EEDQ, Fluka), 3.3 g (0.7 mmol) of the above-described tetracosahydrobromide and 1.70 g (16.8 mmol) of triethylamine are added, and it is stirred overnight at room temperature. The solution is then mixed with acetone, the precipitate is suctioned off, dried, taken up in water, insoluble portions are filtered out, and the filtrate is desalinated with an Amicon$^{(R)}$ YM3 ultrafiltration membrane (cut off 3,000 Da) and low-molecular components are removed. The retentate is then freeze-dried.

Yield: 10.53 g (77% of theory)
H$_2$O content (Karl Fischer)g 9%
Gd determination (AAS): 18.5%
Elementary analysis (relative to anhydrous substance):
Cld: C 41.12 H 5.52 N 12.99 Gd 21.21 Fnd: C 40.95 H 5.62 N 12.78 Gd 21.01

The MALDI-MS shows signals at m/z=about 17,790 (24mer), about 17,180 (23mer) and about 16,540 (22mer).

EXAMPLE 17

32-mer-Dysprosium complex of N-(5-D03A-yl-4-oxo-3-azahexanoyl)-cascade polyamide based on the 32mer amine is described in Example 3c)

8.35 g (1 mmol) of the 32-mer-benzyloxycarbonylamine described in Example 3c) is dissolved in glacial acetic acid and mixed with 33% hydrogen bromide in glacial acetic acid while being stirred. After 3 hours, the incipient precipitation is completed with diethyl ether, the 32-amine-hydrobromide produced is washed with ether, dried in a vacuum (quantitative yield) and used in the following reaction without further purification. 60.96 g (96 mmol, 3X excess) of the Dy complex of 10-(4-carboxy-1-methyl-2-oxo-3-azabutyl)-1,4,7,10-tetraazacyclododecane-1,4,7-triacetic acid described in Example 5 is dissolved in 500 ml of formamide under heat. After cooling to room temperature, 26.1 g (105.6 mmol) of 2-ethoxy-1-ethoxycarbonyl-1,2-dihydroquinoline (EEDQ, Fluka), 1 mmol of the above-described dotriacontahydrobromide and 3.24 g (32 mmol) of triethylamine are added, and it is stirred overnight at room temperature The solution is then mixed with acetone, the precipitate is suctioned off, dried, taken up in water, insoluble portions are filtered out, and the filtrate is desalinated with an Amicon$^{(R)}$ YM3 ultrafiltration membrane (cut off 3,000 Da) and low-molecular components are removed. The retentate is then freeze-dried.

Yield: 19.0 g (75% of theory)
H$_2$O content (Karl Fischer): 6%
Dy determination (AAS): 19.7%
Elementary analysis (relative to anhydrous substance):
Cld: C 39.98 H 5.35 N 13.19 Dy 21.85 Fnd: C 39.83 H 5.26 N 13.28 Dy 21.51

The MALDI-MS shows signals at m/z=about 23,800 (32mer), about 23,200 (31mer) and about 22,600 (30mer).

EXAMPLE OF AN IN VIVO COMPARISON WITH AN EXTRACELLULAR CONTRAST MEDIUM

The suitability of the compound described in Example 1k) as a blood-pool-agent is shown in the following test.

As test animals, five male (Schering-SPF) rats that are 300–350 g in weight are used. Before the test, the abdomen is opened, the intestines are shifted and then the renal vessels (arterial+venous) of both sides are ligated through the rear peritoneum with a surgical needle. Then, the abdominal cavity is closed again. 0.3 ml (respectively 50 mmol/L) of the following contrast medium solution per animal is then administered intravenously: mixture of 1 part each of the compound of Example 1k), named compound 1 below, and the dysprosium complex of 10-(1-hydroxymethyl-2,3-dihydroxypropyl)-1,4,7-tris(carboxymethyl)-1,4,7,10-tetraazacyclododecane, produced analogously to the instructions in European Patent Application EP 448 191, named compound 2 below. Blood samples are taken with a catheter in the common carotid artery at the following times: 15, 30, 45, 60, 90 seconds, 3, 5, 10, 15 minutes p i. In the blood samples obtained, the concentrations of gadolinium (Gd) and dysprosium (Dy) are measured with the aid of atomic emission spectrometry (ICP-AES) in each case in a parallel manner. The portion of the injected contrast medium of compound 1 (Gd) and compound 2 (Dy, comparison substance), remaining in the blood space, can be compared in the same animals by the different marking Since renal excretion is not possible, the decrease of the blood concentration can be attributed only to a dispersion in the blood spaces and to the diffusion in the interstitial tissue.

Results: The diffusion of compound 1 in the interstitium is considerably slowed-down in comparison to an extracellular contrast medium compound 2 (see figure 1).

The extracellular contrast medium (compound 2) diffuses quickly into the interstitial spaces of the body, so that as early as after 3–5 minutes p.i., an equilibrium is reached (displayed by constant blood level). In contrast to this, not only are constantly higher blood concentrations measured with the cascade polymer (compound 1) (reference to smaller volume of distribution), in addition no equilibrium is reached over the entire examination period of 15 minutes (reference to diffusion into interstitial tissue proceeding only very slowly). This means that compound 1 behaves as a blood-pool contrast medium

EXAMPLE OF A LYMPH NODE CONCENTRATION IN GUINEA PIGS

The compound according to the invention that was mentioned under Example 11k was studied 30 minutes to 24 hours after subcutaneous administration (10 μmol of gadolinium/kg of body weight, hind paw s.c.) to stimulated guinea pigs (complete Freund's adjunct; in each case 0.1 ml i.m. in the right and left upper and lower legs; 2 weeks before administration of test substances) with respect to their lymph node concentration in three successive lymph node stations (popliteal, inguinal, iliac). In this connection, the results listed below (determination of the gadolinium concentration by means of ICP-AES) were obtained:

| Time of Lymph Node Removal | Gadolinium Concentration in Three Successive Lymph Node Stations [μmol/l] [% dose/g of tissue] | | | Ratio |
|---|---|---|---|---|
| | Popliteal | Inguinal | Iliac | |
| 30 min p.i. | 921 μmol/l 20.1% | 387 μmol/l 8.5% | 215 μmol/l 4.7% | 10:4.2:2.3 |
| 90 min p.i. | 659 μmol/l 14.4% | 120 μmol/l 2.6% | 68 μmol/l 1.5% | 10:1.8:1.0 |
| 4 h p.i. | 176 μmol/l 3.9% | 79 μmol/l 1.7% | 47 μmol/l 1.0% | 10:4.5:2.7 |
| 24 h p.i. | 62 μmol/l 1.4% | 13 μmol/l 0.3% | 28 μmol/l 0.6% | 10:2.1:4.5 |

We claim:

1. Compounds of general formula II

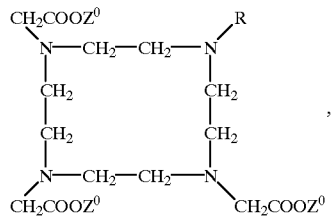

(II)

whereby $Z^o$ stands for a metal ion equivalent of atomic numbers 58–71 and

R stands for a $CHX^1$—CO—NH—$CHY^1$—$(CH_2)_f$—COOH group, in which $X^1$ and $Y^1$, independently of one another, mean a hydrogen atom, a straight-chain or branched $C_1$–$C_7$ alkyl radical, a phenyl or benzyl group and f means numbers 0 to 9.

2. Compounds according to claim 1; characterized in that $Z^o$ stands for a metal ion equivalent of atomic numbers 64, 66 and 70.

3. Compounds according to claim 1, wherein $X^1$ stands for a methyl group.

4. Compounds according to claim 1, wherein $Y^1$ stands for a hydrogen atom.

5. Compounds according to claim 1, wherein f stands for numbers 0, 1 or 2.

6. Compound according to claim 1:

Gadolinium complex of 10-[4-carboxy-1-methyl-2-oxo-3-azabutyl]-1,4,7,10-tetraazacyclododecane-1,4,7-triacetic acid.

7. Process for the production of compounds of general formula II,

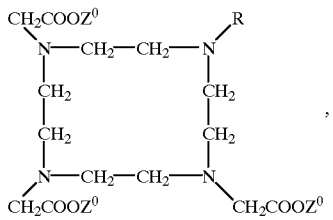

(II)

whereby $Z^o$ stands for a metal ion equivalent of atomic numbers 58–71 and

R stands for a $CHX^1$—CO—NH—$CHY^1$—$(CH_2)_f$—COOH group, in which $X^1$ and $Y^1$, independently of one another, mean a hydrogen atom, a straight-chain or branched $C_1$–$C_7$ alkyl radical, a phenyl or benzyl group and f means numbers 0 to 9, wherein compounds of general formula III

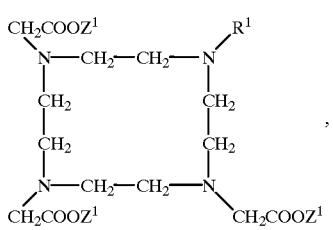

(III)

in which

R' has the meaning of R, whereby the carboxyl group contained therein is optionally present in protected form and $Z^1$ stands for a hydrogen atom or a carboxyl protective group, after cleavage of the optionally present carboxyl protective groups, are reacted in a way known in the art with a metal oxide or metal salt of an element of atomic numbers 58–71.

8. A method of NMR diagnosis comprising administering to a subject one of the compounds of claim 1 and subsequently performing and NMR diagnosis procedure.

9. A method of diagnostic radiology comprising administering to a subject one of the compounds of claim 1 and subsequently performing a diagnostic imaging procedure.

* * * * *